(12) United States Patent
Takahashi et al.

(10) Patent No.: US 9,447,232 B2
(45) Date of Patent: Sep. 20, 2016

(54) CARRIER POLYMER PARTICLE, PROCESS FOR PRODUCING THE SAME, MAGNETIC PARTICLE FOR SPECIFIC TRAPPING, AND PROCESS FOR PRODUCING THE SAME

(71) Applicant: JSR CORPORATION, Chuo-ku (JP)

(72) Inventors: Masayuki Takahashi, Tsukuba (JP); Tetsuo Fukuta, Tsuchiura (JP); Kiyoshi Kasai, Kawasaki (JP); Toshihiro Ogawa, Tsukuba (JP); Satoshi Katayose, Tsukubamirai (JP); Kouji Tamori, Tsuchiura (JP); Kinji Yamada, Tsukuba (JP)

(73) Assignee: JSR CORPORATION, Minato-ku (JP)

( * ) Notice: Subject to any disclaimer, the term of this patent is extended or adjusted under 35 U.S.C. 154(b) by 518 days.

(21) Appl. No.: 13/763,236

(22) Filed: Feb. 8, 2013

(65) Prior Publication Data

US 2013/0149538 A1 Jun. 13, 2013

Related U.S. Application Data

(62) Division of application No. 11/914,986, filed as application No. PCT/JP2006/309810 on May 17, 2006, now abandoned.

(30) Foreign Application Priority Data

May 20, 2005 (JP) ................... 2005-147824
Sep. 22, 2005 (JP) ................... 2005-276052
Nov. 28, 2005 (JP) ................... 2005-342167

(51) Int. Cl.
*G01N 33/543* (2006.01)
*C08G 63/91* (2006.01)
(Continued)

(52) U.S. Cl.
CPC ............. *C08G 63/91* (2013.01); *B32B 5/16* (2013.01); *G01N 33/53* (2013.01); *G01N 33/5434* (2013.01); *G01N 33/54353* (2013.01); *Y10T 428/2982* (2015.01); *Y10T 428/2998* (2015.01)

(58) Field of Classification Search
CPC .............. G01N 33/5434; G01N 33/54353; Y10T 428/2982; Y10T 428/2998; B32B 5/16; C08G 63/09
USPC .................................................. 436/518, 525
See application file for complete search history.

(56) References Cited

U.S. PATENT DOCUMENTS 4,230,685 A 10/1980 Senyei et al.
4,452,773 A 6/1984 Molday
(Continued)

FOREIGN PATENT DOCUMENTS

JP 57 24369 5/1982
JP 61 215602 9/1986
(Continued)

OTHER PUBLICATIONS

"High Swelling of latex Particles without the Utilization of Swelling Agents", Journal of Polymer Science: Polymer Letters Edition, vol. 21, pp. 937-943, 1983.

(Continued)

*Primary Examiner* — Mark Shibuya
*Assistant Examiner* — Pensee Do
(74) *Attorney, Agent, or Firm* — Oblon, McClelland, Maier & Neustadt, L.L.P.

(57) ABSTRACT

A process for producing carrier polymer particles comprising covering the surface of organic polymer particles having a particle diameter of 0.1 to 20 micrometers with a saccharide by chemically bonding the organic polymers and the saccharide.

8 Claims, 3 Drawing Sheets

(51) Int. Cl.
  *G01N 33/53* (2006.01)
  *B32B 5/16* (2006.01)

(56) References Cited

U.S. PATENT DOCUMENTS

| | | | |
|---|---|---|---|
| 5,166,077 A * | 11/1992 | Kihara et al. | 436/534 |
| 5,204,096 A | 4/1993 | Neurath et al. | |
| 5,213,895 A | 5/1993 | Hirai et al. | |
| 5,236,824 A | 8/1993 | Fujiwara et al. | |
| 5,238,811 A | 8/1993 | Fujiwara et al. | |
| 6,033,862 A | 3/2000 | Matsuda et al. | |
| 6,767,635 B1 | 7/2004 | Bahr et al. | |
| 7,179,660 B1 | 2/2007 | Kirakossian et al. | |
| 7,645,614 B2 | 1/2010 | Tanaka et al. | |
| 7,732,051 B2 | 6/2010 | Tamori et al. | |
| 7,981,512 B2 | 7/2011 | Tamori et al. | |
| 8,404,494 B2 | 3/2013 | Tamori et al. | |
| 2005/0192381 A1 | 9/2005 | Bringley et al. | |
| 2006/0105549 A1 | 5/2006 | Duineveld et al. | |
| 2006/0223126 A1 | 10/2006 | Tamori et al. | |
| 2006/0226013 A1 | 10/2006 | Decre et al. | |
| 2007/0099814 A1 | 5/2007 | Tamori et al. | |
| 2007/0224424 A1 | 9/2007 | Tamori et al. | |
| 2008/0160167 A1 | 7/2008 | Tamori et al. | |
| 2008/0160277 A1 | 7/2008 | Tamori et al. | |
| 2009/0014682 A1 | 1/2009 | Takahashi et al. | |
| 2010/0105879 A1 | 4/2010 | Katayose et al. | |
| 2010/0204424 A1 | 8/2010 | Tamori et al. | |
| 2011/0184155 A1 | 7/2011 | Takahashi et al. | |
| 2011/0233454 A1 | 9/2011 | Tamori et al. | |

FOREIGN PATENT DOCUMENTS

| | | |
|---|---|---|
| JP | 61 215603 | 9/1986 |
| JP | 61 215604 | 9/1986 |
| JP | 1 121342 | 5/1989 |
| JP | 1-272970 | 10/1989 |
| JP | 4 21637 | 1/1992 |
| JP | 7 238105 | 9/1995 |
| JP | 3086427 | 7/2000 |
| JP | 2001 513203 | 8/2001 |
| JP | 3292721 | 3/2002 |
| JP | 2003-509034 | 3/2003 |
| JP | 2003-130880 | 5/2003 |
| JP | 2003 526786 | 9/2003 |
| JP | 2003 277455 | 10/2003 |
| JP | 2005-69955 | 3/2005 |
| JP | 8 502443 | 3/2006 |
| WO | WO0167105 A1 * | 9/2001 |
| WO | 2004 025297 | 3/2004 |
| WO | 2004 040305 | 5/2004 |
| WO | 2005 097844 | 10/2005 |

OTHER PUBLICATIONS

Harding, A receptor for the immuno-suppressant FK506 is a cis-trans peptidyl-prolyl isomerase, Letters to Nature, vol. 341, pp. 758-760, 1989.

The 4th edition of Experimental Chemistry Lecture, vol. 22, pp. 45-47, 1992.

The 4th edition of Experimental Chemistry Lecture, vol. 22, pp. 138-144, 1992.

The 4th edition of Experimental chemistry lecture, vol. 22, pp. 259-271, 1992.

Office Action issued Oct. 26, 2011, in Japanese Patent Application No. 2005-147824 (with English-language translation).

U.S. Appl. No. 13/740,763, filed Jan. 4, 2013, Takahashi, et al.

* cited by examiner lane1 : PROTEINS TRAPPED BY PARTICLES OF EXAMPLE 1 lane2 : PROTEINS TRAPPED BY PARTICLES OF EXAMPLE 2 lane3 : PROTEINS TRAPPED BY PARTICLES OF COMPARATIVE EXAMPLE 1 lane4 : REFERENCE AFP 20 ng lane5 : REFERENCE AFP 50 ng lane6 : REFERENCE AFP 100 ng lane7 : Mw Marker

LANE1 LANE2 LANE3 LANE4 LANE5 LANE6

US 9,447,232 B2

CARRIER POLYMER PARTICLE, PROCESS FOR PRODUCING THE SAME, MAGNETIC PARTICLE FOR SPECIFIC TRAPPING, AND PROCESS FOR PRODUCING THE SAME

CROSS REFERENCE TO RELATED APPLICATION

This application is a Divisional application of U.S. application Ser. No. 11/914,986, filed on Mar. 3, 2008, which is a 371 of PCT/JP06/309810, filed on May 17, 2006, and claims priority to the following applications: Japanese Patent Application No. 2005-147824, filed on May 20, 2005, Japanese Patent Application No. 2005-276052, filed on Sep. 22, 2005, and Japanese Patent Application No. 2005-342167, filed Nov. 28, 2005.

TECHNICAL FIELD

The present invention relates to carrier polymer particles in which the surface of organic polymer particles are covered with a saccharide, a process for producing the same, magnetic particles for specific trapping, and a process for producing the same.

BACKGROUND ART

In recent years, attempts have been actively made in fields such as drug discovery to find molecules having specific interaction with a certain specific molecule by utilizing intermolecular interaction. Specifically, immobilizing a molecule (probe molecule) having interaction on a support, and trapping and purifying another molecule (target material) by utilizing a specific interaction is widely carried out.

For example, the discovery of the intracellular binding protein FKBP12 of the immunosuppressant FK506 using an affinity resin (Nature, 341, 758, 1989) has been known. A porous gel such as agarose is commonly used as such affinity resin. However, when using a porous gel, the so-called phenomenon nonspecific adsorption in which molecules other than the target molecule are adsorbed on the affinity resin arises and thus, the problem that separation and purification of the target molecule is difficult arises. A certain proportion among the probe molecules bond internally to the porous gel and as a result of such probe molecules having insufficient interaction with the target material, the problem arises that trapping efficiency of the target material is reduced.

As a solution to such nonspecific adsorption, microspheres made from a styrene/glycidyl methacrylate polymer, of which the surface is covered with glycidyl methacrylate, and a biologically-related material bonded to the polymer through a spacer have been proposed (JP-B-3086427 and JP-B-3292721). Also disclosed are particles having a hydrophilic spacer introduced on the surface (WO 2004/025297 A1 and WO 2004/040305A1), and the like. However, none of these have a sufficient effect in lowering nonspecific adsorption. Support particles having still smaller nonspecific adsorption are desired. Also, the efficiency of trapping the target material of these particles is not sufficient.

On the other hand, as biologically-related material carrier polymer particles which are sensitized by a chemical bonding method, carboxyl group-modified polystyrene particles are widely used. However, since the polystyrene particles generally have significant capability of adsorbing other biologically-related materials (nonspecific adsorption) which are not target materials existing in the test sample, the performance of the sensitized particles is inhibited, posing a serious obstacle to use of the particles. In contrast, a blocking method, in which the surface of the particles is first sensitized with the target biologically-active material and a protein having little damage such as bovine serum albumin (BSA) is adsorbed on the remaining particle surface, has difficulty in fully preventing nonspecific adsorption. Also, although it is known that performance of polystyrene particles as biologically-related material carrier particles can be improved by copolymerizing a styrene sulfonate or an acrylic ester having a polyalkylene oxide side chain represented by the formula $(CH_2CH_2O)_n$ or $(CH_2CHCH_3O)_m$ or by hydrolyzing fragments of persulfate initiator bonded to the particles by heat treatment in an alkaline aqueous solution after emulsion polymerization of the particles, the nonspecific adsorption is not sufficiently prevented. Also, the efficiency of trapping the target material of these particles is not sufficient.

DISCLOSURE OF THE INVENTION

An object of the invention is to provide carrier polymer particles which have very small nonspecific absorption of biological materials such as proteins and a process for producing the same.

Another object of the invention is to provide carrier polymer particles which have very small nonspecific absorption of biologically-related materials such as proteins and which have a high trapping efficiency of the target material, and a process for producing the same.

A further object of the invention is to provide magnetic particles for specific trapping which have very small nonspecific absorption of biologically-related materials such as proteins, peptides, nucleic acids, and cells and a process for producing the same.

Carrier polymer particles according to a first aspect of the invention comprise organic polymer particles having a particle diameter of 0.1 to 20 micrometers and a saccharide with which the surface of the organic polymer particles is covered, wherein the organic polymer particles and the saccharide are chemically bonded.

In the carrier polymer particles, the saccharide may be a polysaccharide.

In the carrier polymer particles, the saccharide may be carboxymethylated.

In the carrier polymer particles, the organic polymer particles and the saccharide may be chemically bonded by a bonding group including at least one of an amide bond and an ester bond.

A process for producing carrier polymer particles according to a second aspect of the invention comprises covering the surface of organic polymer particles having a particle diameter of 0.1 to 20 micrometers with a saccharide by chemically bonding the organic polymers and the saccharide.

When chemically bonding in the process for producing carrier polymer particles, the organic polymer particles have a first functional group and the saccharide has a second functional group, and the organic polymer particles and the saccharide may be chemically bonded by reacting the first functional group and the second functional group.

In the process for producing carrier polymer particles, the first functional group may be at least one functional group selected from the group consisting of a carboxyl group, an epoxy group, an amino group, and a tosyl group.

A process for producing carrier polymer particles according to a third aspect of the invention comprises:

covering organic polymer particles having a particle diameter of 0.1 to 20 micrometers and a functional group having reactivity with a carboxyl group with a saccharide having a carboxyl group by chemically bonding the organic polymer particles and the saccharide; and treating the organic polymer particles of which the surface has been covered with the saccharide with a basic solution.

In the process for producing carrier polymer particles, the saccharide may be a polysaccharide.

In the process for producing the carrier polymer particles, the chemically bonding may be achieved by a bonding group including at least one of an amide bond and an ester bond.

In the process for producing carrier polymer particles, the functional group having reactivity with the carboxyl group may be at least one functional group selected from the group consisting of an amino group, a hydroxyl group, and an epoxy group.

The process for producing the carrier polymer particles may further comprise chemically bonding a probe for specifically trapping a target material to the saccharide.

Magnetic particles for specific trapping according to a fourth aspect of the invention comprise magnetic particles having a particle diameter of 0.1 to 20 micrometers and a saccharide, wherein the magnetic particles and the saccharide are chemically bonded and a probe for specifically trapping a target material is bonded to the saccharide.

The saccharide of the magnetic particles for specific trapping may be a polysaccharide.

The saccharide of the magnetic particles for specific trapping may be carboxymethylated.

The magnetic particles for specific trapping and the saccharide may be chemically bonded by a bonding group including at least one of an amide bond and an ester bond.

The magnetic particles of the magnetic particles for specific trapping are obtained by polymerization of a polymer layer on the magnetic material layer of mother particles comprising nuclear particles and a magnetic material layer formed on the surface of the nuclear particles, and the magnetic material layer may include at least one of $Fe_2O_3$ and $Fe_3O_4$.

The probe of the magnetic particles for specific trapping may be at least one selected from proteins, peptides, nucleic acids, glycoside compounds, and synthetic chemical materials.

A process for producing magnetic particles for specific trapping according to a fifth aspect of the invention comprises:

chemically bonding magnetic particles having a particle diameter of 0.1 to 20 micrometers and a saccharide; and chemically bonding a probe for specifically trapping a target material to the saccharide.

When chemically bonding the magnetic particles and the saccharide in the process for producing carrier polymer particles, the magnetic particles have a first functional group and the saccharide has a second functional group, and the magnetic particles and the saccharide may be chemically bonded by reacting the first functional group and the second functional group.

In the process for producing magnetic particles for specific trapping, the first functional group may be at least one functional group selected from the group consisting of a carboxyl group, an epoxy group, an amino group, and a tosyl group.

The carrier polymer particles possess the characteristic of having little nonspecific adsorption due to the organic polymer particles having a particle diameter of 0.1 to 20 micrometers, the saccharide covering the surface of the organic polymer particles, and the organic polymer and the saccharide are chemically bonded. Thus, the separation and the purification of target molecules can be easily carried out.

According to the process for producing carrier polymer particles, carrier polymer particles having little nonspecific adsorption and a high efficiency of trapping a target material can be obtained by covering the organic polymer particles with a particle diameter of 0.1 to 20 micrometers, which has a functional group having reactivity with a carboxyl group, with a saccharide having a carboxyl group by chemically bonding the organic polymer particles and the saccharide, and treating the organic polymer particles, of which the surface has been covered with the saccharide, with a basic solution. Thus, the separation and the purification of target molecules can be easily carried out.

Furthermore, the magnetic particles for specific trapping possess the characteristic of having little nonspecific adsorption, due to the use of the magnetic particles having a particle diameter of 0.1 to 20 micrometers, inclusion of a saccharide, the magnetic particles are chemically bonded to the saccharide, and a probe for specifically trapping a target material is chemically bonded to the saccharide. Thus, the separation and the purification of target molecules can be easily carried out.

BEST MODE FOR CARRYING OUT THE INVENTION

Figure 1:
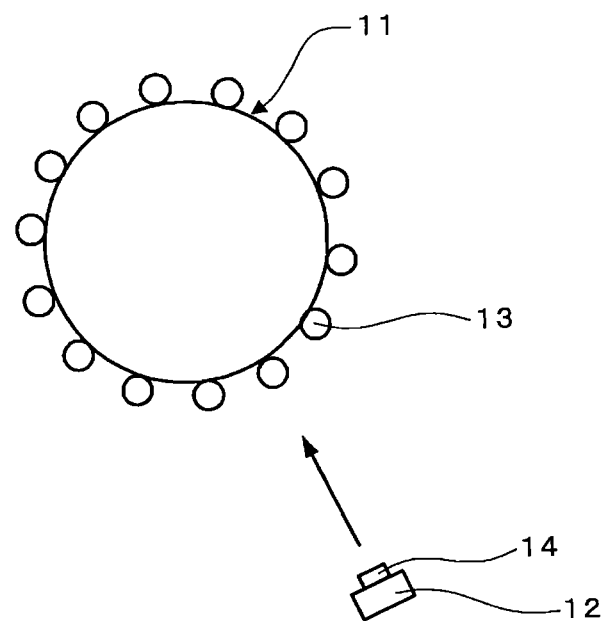
FIG. 1 is a diagram showing an example of a process for producing carrier polymer particles according to the first and second embodiments of the invention.

The carrier polymer particles, the process for producing the same, the magnetic particles for specific trapping, and the process for producing the same of the invention are explained in detail below.

1. First Embodiment 1-1. Carrier Polymer Particles

The carrier polymer particles according to the first embodiment of the invention comprise organic polymer particles having a particle diameter of 0.1 to 20 micrometers and a saccharide with which the surface of the organic polymer particles is covered. Also, the organic polymer particles and the saccharide are chemically bonded in the carrier polymer particles according to this embodiment. Although not limited, it is preferable that the chemically bonding is achieved by a bonding group including at least one of an amide bond and an ester bond.

Although it is possible to use the carrier polymer particles according to the present embodiment as they are, they can also be used as a dispersion liquid in which the particles are dispersed in a dispersion medium in order to efficiently carry out a reaction with a compound. As examples of the dispersion medium, water; alcohols such as methanol, ethanol, propanol, isopropyl alcohol, n-butyl alcohol, isobutyl alcohol, sec-butyl alcohol, and tert-butyl alcohol; ethylene glycol derivatives such as ethylene glycol, ethylene glycol monomethyl ether, ethylene glycol monoethyl ether, ethylene glycol monopropyl ether, ethylene glycol monobutyl ether, ethylene glycol monoethyl ether acetate, diethylene glycol monomethyl ether, diethylene glycol monoethyl ether, diethylene glycol dimethyl ether, and diethylene glycol diethyl ether; propylene glycol derivatives such as propylene glycol, propylene glycol monomethyl ether, propylene glycol monoethyl ether, propylene glycol monopropyl ether, propylene glycol monobutyl ether, and propylene glycol monomethyl ether acetate; ketones such as acetone, methyl ethyl ketone, methyl isobutyl ketone, methyl amyl ketone, diisobutyl ketone, and cyclohexanone; esters such as ethyl acetate, butyl acetate, isobutyl acetate, ethyl lactate, and gamma-butyl lactone; amides such as N,N-dimethylformamide, N,N-dimethylacetamide, and N-methylpyrrolidone; dimethyl sulfoxide; and aromatic hydrocarbons such as toluene and xylene can be given.

The particle diameter of the carrier polymer particles according to the present embodiment are preferably 0.1 to 17 micrometers, and more preferably 1 to 10 micrometers. When the particle diameter is less than 0.1 micrometer, since separation using centrifugal separation or the like takes a long time and separation of the washing solvent such as water and the particles is insufficient, there are situations in which the removal of non-target molecules (for example, biologically-related materials such as proteins) is insufficient and thus, sufficient purification is not possible. In contrast, since particles with a diameter exceeding 17 micrometers reduces the surface area of the particles, there may be situations in which the trapped amount of the biologically-related material such as proteins, which is the target, is small.

Next, the constituting elements of the carrier polymer particles according to the embodiment are explained in detail.

1-1-1. Organic Polymer Particles

The average particle diameter of the organic polymer particles used in the present embodiment is 0.1 to 20 micrometers, more preferably 0.3 to 15 micrometers, and most preferably 1 to 10 micrometers. Also, the coefficient of variation of the organic polymer particles used in the invention is normally 30% or less, preferably 20% or less, and more preferably 10% or less.

In the embodiment, the organic polymer particles may be used as base particles of the carrier polymer particles according to the embodiment. Organic polymer particles are suitable as base particles, since it is easy to cover the surface of organic polymer particles with a saccharide which is bonded by chemically bonding. Also, magnetic particles may be used as the organic polymer particles.

As explained above, when the carrier polymer particles according to the embodiment are dispersed in a solvent, nonspecific adsorption of biologically-related materials such as proteins increases if the organic polymer particles are dispersed in a dispersion medium or the organic polymer particles swell by the solvent. For this reason, it is desirable that the organic polymer particles do not dissolve in the dispersion medium. Here, an aqueous medium may be used as the dispersion medium, for example. Here, aqueous medium means water or a mixture of water and a solvent which are dissolved in water (for example, alcohols and alkylene glycol derivatives).

Vinyl polymers are particularly preferable as the polymer constituting the organic polymer particles. As examples of the vinyl monomers constituting the vinyl polymer, aromatic vinyl monomers such as styrene, alpha-methyl styrene, halogenated styrene, and divinylbenzene; vinyl esters such as vinyl acetate and vinyl propionate; unsaturated nitriles such as acrylonitrile; ethylenic unsaturated carboxylic acid alkyl esters such as methyl acrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, cyclohexyl acrylate, and cyclohexyl methacrylate; polyfunctional (meth)acrylates such as ethylene glycol diacrylate, ethylene glycol dimethacrylate, trimethylol propane triacrylate, and trimethylol propane trimethacrylate; and (meth)acrylates having a functional group such as glycidyl acrylate, glycidyl methacrylate, 2-hydroxyethyl acrylate, and 2-hydroxyethyl methacrylate can be given. The vinyl polymer may be a homopolymer or may be a copolymer comprising two or more monomers selected from the above-mentioned vinyl monomers. Also, a copolymer of the above-mentioned vinyl monomers and copolymerizable monomers such as conjugated diolefins such as butadiene and isoprene, acrylic acid, methacrylic acid, itaconic acid, acrylamide, methacrylamide, N-methylol acrylamide, N-methylol methacrylamide, diallyl phthalate, allyl acrylate, and allyl methacrylate can also be used.

The magnetic particles are general particulate materials which can be magnetically collected and include fine particles of a magnetic material. When the organic polymer particles used in this embodiment are magnetic particles, the carrier polymer particles according to the embodiment can be used as magnetic particles usable in applications described later as examples.

If the particle diameter of the magnetic particles is less than 0.1 micrometer, it may take a long time for separation and purification using magnetism; and if more than 20 micrometers, the amount of trapped target material such as proteins may be small due to the surface area becoming smaller.

Although the internal composition of the magnetic particles may be homogeneous, most magnetic materials making up the homogeneous magnetic particles with a particle diameter in the above-mentioned preferable range are paramagnetic. If repeatedly separated and purified by magnetism, the magnetic particles may lose their capability of being redispersed in dispersion media. For this reason, it is preferable that the magnetic particles have a heterogeneous internal composition containing fine particles of a magnetic material exhibiting small residual magnetization. As the inner structure of the magnetic particles having such a heterogeneous internal composition, a structure in which the fine particles of a magnetic material are dispersed in a continuous phase of a non-magnetic material such as a polymer, a structure consisting of a secondary aggregate of fine particles of a magnetic material as a core and a non-magnetic material such as a polymer layer as a shell, a structure consisting of a non-magnetic material such as a polymer (non-magnetic nuclear particles) as a core and a secondary aggregate material of fine particles of a magnetic material as a shell, and the like can be given. As the polymer which is included in the magnetic particles, the polymers described above as the polymer forming the organic polymer particles may be used. In the case of the structure in which the inner structure consists of a core of a non-magnetic material such as a polymer (non-magnetic nuclear particles) and a shell of a secondary aggregate of fine particles of a magnetic material, it is preferable that a polymer layer be further formed on the outermost layer. As the polymer which is used for the outermost layer, the polymers described above as the polymer forming the organic polymer particles as the base particles may be used.

The organic polymer particles of this embodiment may be produced by a general method such as emulsion polymerization, soap-free polymerization, and suspension polymerization. When the organic polymer particles are magnetic particles, such organic polymer particles may be produced by, for example, mixing the non-magnetic material nuclear particles with the fine particles of a magnetic material and causing the fine particles of a magnetic material to be physically adsorbed on the surface of the non-magnetic material nuclear particles. In this embodiment, "physical adsorption" refers to adsorption not involving a chemical reaction. As the principle of "physical adsorption", hydrophobic/hydrophobic adsorption, molten bonding or adsorption, fusion bonding or adsorption, hydrogen bonding, Van der Waals bonding, and the like can be given, for example.

More specifically, the organic polymer particles may be obtained by, for example, suspension polymerization of the above vinyl monomer or polymer bulk shattering. For example, the organic polymer particles can be obtained by a two-stage swelling polymerization method using seed particles described in JP-B-57-24369, the polymerization method described in J. Polym. Sci., Polymer Letter Ed., 21, 937 (1963), and the methods described in JP-A-61-215602, JP-A-61-215603, and JP-A-61-215604.

The magnetic particles can also be prepared by a method utilizing hydrophobic/hydrophobic adsorption as mentioned above. For example, a method selecting non-magnetic nuclear particles and fine particles of a magnetic material, each having a hydrophobic or hydrophobized surface, and dry-blending these non-magnetic nuclear particles and fine particles of a magnetic material, and a method sufficiently dispersing the non-magnetic nuclear particles and the fine particles of a magnetic material in a solvent (such as toluene or hexane) with good dispersibility without damaging both particles, followed by vaporization of the solvent while mixing can be given. Alternatively, the magnetic particles may be produced by a method realizing complexing on non-magnetic nuclear particles and fine particles of a magnetic material by physically applying a strong external force. As examples of the method for physically applying a strong force, a method using a mortar, an automatic mortar, or a ball mill; a blade-pressuring type powder compressing method; a method utilizing a mechanochemical effect such as a mechanofusion method; and a method using an impact in a high-speed air stream such as a jet mill, a hybridizer, or the like can be given. In order to efficiently produce a firmly bound complex, a strong physical adsorption force is desirable. As the method, stirring using a vessel equipped with a stirrer at a peripheral velocity of stirring blades of preferably 15 m/sec or more, more preferably 30 m/sec or more, and still more preferably from 40 to 150 m/sec can be given. If the stirring blade peripheral velocity is less than 15 m/sec, sufficient energy for causing fine particles of a magnetic material to be adsorbed on the surface of non-magnetic nuclear particles may not be obtained. Although there are no specific limitations to the upper limit of the peripheral speed of the stirring blades, the upper limit of the peripheral speed is determined according to the apparatus to be used, energy efficiency, and the like.

1-1-2. Saccharide

As examples of the saccharide used for the carrier polymer particles according to this embodiment, monosaccharides, such as furanoses such as fructose, arabinose, xylose, ribose, and deoxyribose, pyranoses such as glucose, mannose, and galactose, and septanoses; disaccharides such as trehalose, lactose, kojibiose, nigerose, maltose, isomaltose, sophorose, laminaribiose, cellobiose, and gentiobiose; and polysaccharides such as starch, amylose, amylopectin, dextrin, glycogen, cyclodextrin, cellulose, agarose, alginic acid, inulin, glucomannan, chitin, chitosan, and hyaluronic acid can be given. In order to cover the surface of organic polymer particles by the chemical bond of the organic polymer particles and the saccharide, a polysaccharide with a high molecular weight is preferable from the viewpoint of coating efficiency. A saccharide of which at least a part of the functional group (such as a hydroxyl group, an amino group, and a carboxyl group) has been modified, such as carboxymethylcellulose and carboxymethyldextran, may be used. The modification may be made in multiple stages, if necessary. More preferably, a carboxymethylated saccharide such as carboxymethylcellulose or carboxymethyldextran can be used.

1-2. Process for Producing Carrier Polymer Particles

The process for producing carrier polymer particles of this embodiment comprises covering the surface of organic polymer particles having a particle diameter of 0.1 to 20 micrometers with a saccharide by chemically bonding the organic polymers and the saccharide.

In this embodiment, a general chemical reaction may be used for chemically bonding the organic polymer particles with a saccharide without any particular limitations.

Figure 2:
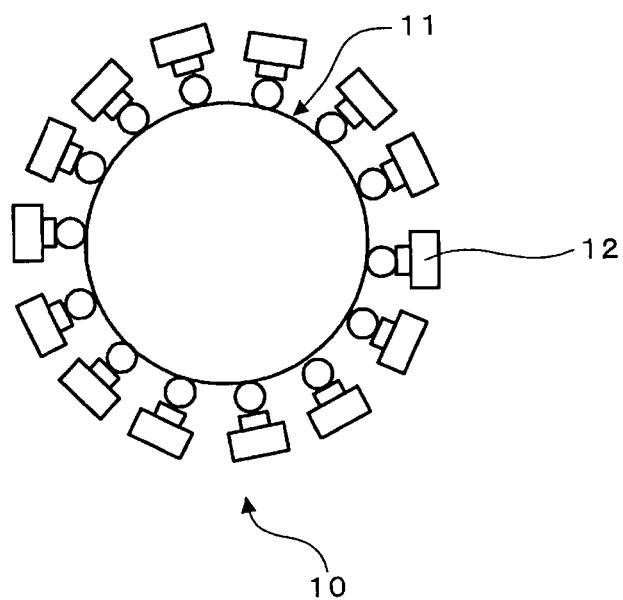
FIG. 2 is a diagram showing an example of carrier polymer particles according to the first and second embodiments of the invention.

FIG. 1 is a diagram showing the process for producing the carrier polymer particles according to this embodiment. FIG. 2 is a diagram showing the process for producing the carrier polymer particles according to this embodiment, wherein a carrier polymer particle 10 of the embodiment produced by the process shown in FIG. 1 is shown.

For example, as shown in FIG. 1, the organic polymer particle 11 used for producing the carrier polymer particles according to this embodiment may have a plurality of functional groups 13 (first functional groups) on the surface. The first functional groups 13 may be functional groups introduced when the particle shape of the organic polymer particle 11 is formed or functional groups obtained by converting the functional groups after the particle shape of the organic polymer particle 11 has been formed. The conversion of functional groups may be carried out two or more times. Although not particularly limited, when the functional group introduced when forming the particle shape of the organic polymer particle 11 is an epoxy group, an amino group produced by reacting the epoxy group with a large excess amount of ammonia or an appropriate diamine compound may be the first functional group, or when the functional group introduced when forming the particle shape of the organic polymer particle 11 is a hydroxyl group, for example, an amino group produced by converting the hydroxyl group into a tosyl group and reacting the tosyl group with a large excess amount of an appropriate diamine compound may be the first functional group 13. For example, in the organic polymer particles Am-1 to Am-5 respectively obtained in the later-described Experimental Examples 1 to 3, and Experimental Examples 5 to 6, the first functional group 13 may be the amino group.

The saccharide 12 used for producing the carrier polymer particles according to this embodiment may have a plurality of functional groups (second functional groups) 14 in the molecule. The functional group may be produced by converting the functional group of a saccharide.

As the functional group which can be used as the first functional group 13 and/or the second functional group 14, a carboxyl group, a hydroxyl group, an epoxy group, an amino group, a mercapto group, a vinyl group, an allyl group, an acrylic group, a methacryl group, a tosyl group, an azido group, and the like can be given. The first functional group 13 and the second functional group 14 are reactive with each other. Although not particularly limited, when the first functional group 13 is an epoxy group, for example, the second functional group 14 may be an amino group, or when the first functional group 13 is an amino group, for example, the second functional group 14 may be a carboxyl group.

It is possible to chemically bond the organic polymer particle 11 with a saccharide 12 by reacting the first functional group 13 and the second functional group 14 (see FIG. 2), whereby the carrier polymer particle 10 according to this embodiment can be obtained.

After preparation according to the above-described process, the carrier polymer particles of this embodiment can be used as carrier particles after adjusting the pH and washing the surface by a purification process such as dialysis, ultrafiltration, and centrifugation, as required.

1-3. Application

The carrier polymer particles of this embodiment are used as chemical bonding carrier polymer particles in the drug discovery field and also as chemical bonding carrier polymer particles for diagnostic agent.

More particularly, the carrier polymer particles of this embodiment can be used for selecting and purifying proteins and the like exhibiting specific interactions with a chemical compound to be analyzed by immobilizing such a chemical compound to be analyzed by chemical bonding and analyzing and/or measuring the specific interactions using intermolecular interactions with the proteins and the like.

In addition, the carrier polymer particles of this embodiment can also be used as biologically-related material carrier polymer particles for sensing proteins such as an antibody, an antigen, an enzyme, and a hormone, nucleic acids such as DNA and RNA, and biologically-related glycoside compounds (hereinafter referred to collectively as "biologically-related material") on the surface of particles by a chemical bonding method.

The applications of the carrier polymer particles of this embodiment are not limited to the above-mentioned applications of chemical bonding carrier polymer particles in the drug discovery field and chemical bonding carrier polymer particles for diagnostic drugs. The carrier polymer particles can be used in a wide variety of fields such as biologically-related fields, paints, papers, electrophotography, cosmetics, medical supplies, agricultural chemicals, foods, and catalysts.

2. Second Embodiment 2-1. Process for Producing Carrier Polymer Particles

The process for producing carrier polymer particles according to the second embodiment comprises covering organic polymer particles with a particle diameter of 0.1 to 20 micrometers, which has a functional group having reactivity with a carboxyl group, with a saccharide having a carboxyl group by chemically bonding the organic polymer particles and the saccharide (a first step), and treating the organic polymer particles, of which the surface has been covered with the saccharide, with a basic solution (a second step).

The first step and second step in the process for producing the carrier polymer particles according to the embodiment will be explained in detail.

2-1-1. First Step

The functional group which has reactivity with a carboxyl group which exists in the organic polymer particles in the first step of this embodiment is at least one functional group selected from the group consisting of an amino group, a hydroxyl group, and an epoxy group, preferably at least one functional group selected from the group consisting of an amino group and a hydroxyl group, and more preferably an amino group.

In the first step of this embodiment, a general chemical reaction may be used for chemically bonding the organic polymer particles to a saccharide without any particular limitations. The particles may be chemically bonded to the saccharide by a bonding group including at least one of an amide bond and an ester bond.

FIG. 1 is a diagram showing the first step of the process for producing carrier polymer particles according to this embodiment, and FIG. 2 is a diagram showing a example of the carrier polymer particles produced in the first step.

For example, as shown in FIG. 1, the organic polymer particle 11 used for producing the carrier polymer particles according to this embodiment has functional groups 13, which are reactive with a carboxyl group, on the surface. The functional groups 13 which are reactive with a carboxyl group may be introduced when the particle shape of the organic polymer particle 11 is formed, or may be obtained by converting a certain group after the particle shape of the organic polymer particle 11 has been formed. The conversion of functional groups may be carried out two or more times. For example, when the functional group introduced when forming the shape of the organic polymer particle 11 is an epoxy group, an amino group produced by reacting the epoxy group with a large excess amount of ammonia or an appropriate diamine compound may be the functional groups 13 which are reactive with a carboxyl group, or when the functional group introduced when forming the shape of the organic polymer particle 11 is a hydroxyl group, an amino group produced by converting the hydroxyl group into a tosyl group and reacting the tosyl group with a large excess amount of an appropriate diamine compound may be the functional groups 13 which are reactive with a carboxyl group. For example, in the organic polymer particles Am-1 to Am-5 respectively obtained in the later-described Experimental Examples 1 to 3, and Experimental Examples 5 to 6, the functional group 13 which is reactive with a carboxyl group is the amino group.

The saccharide 12 used for producing the carrier polymer particles according to this embodiment may have one carboxyl group 14 or a plurality of carboxyl groups 14 in the molecule. The carboxyl group 14 may be a group produced by converting a specific functional group of the saccharide 12.

As an example of the group which can be used as the functional group 13 reactive with a carboxyl group, an amino group can be given. As mentioned above, the amino group may be converted from another group (such as a hydroxyl group or an epoxy group) which is introduced when the particle shape of the organic polymer particles are formed. The functional group 13 reactive with a carboxyl group and the carboxyl group 14 are reactive with each other. Although not limited, when the functional group 13 having reactivity with a carboxyl group is at least one selected from the group consisting of an amino group, a hydroxyl group, and an epoxy group, for example, this functional group 13 has reactivity with the carboxyl group 14.

In FIG. 1, the organic polymer particle 11 and the saccharide 12 can chemically bond by reacting the functional group 13 having reactivity with a carboxyl group and the carboxyl group 14.

A general method can be used for this chemical bonding without specific limitations. For example, when the group having reactivity with a carboxyl group is an epoxy group, an ester can be produced by directly reacting them. When the group having reactivity with a carboxyl group is a hydroxyl group, an esterification method using various condensing agents can be used (The 4th edition of Experimental Chemistry Lecture Vol. 22, pp 45-47, 1992). When the group having reactivity with a carboxyl group is an amino group, an amidation method using various condensing agents commonly used in organic synthesis (The 4th edition of Experimental Chemistry Lecture Vol. 22, pp 139-144, 1992) and various methods used for forming a peptide bond in peptide synthesis (The 4th edition of Experimental Chemistry Lecture Vol. 22, pp 259-271, 1992) can be used.

After the organic polymer particle 11 and the saccharide 12 have been chemically bonded and the surface of the organic polymer particle 11 is covered with the saccharide 12 (see FIG. 2), an excess amount of the saccharide existing in the reaction system (not shown in the drawing) may be physically adsorbed in the saccharide 12 which chemically bonded to the organic polymer particle 11 by hydrogen bonds and the like between carboxyl group and carboxyl group, carboxyl group and hydroxyl group, and/or hydroxyl group and hydroxyl group. In order to sufficiently cover the surface of the organic polymer particle 11 with a chemically bonded saccharide 12, it is necessary to use an excess amount of a saccharide. Therefore, occurrence of physical adsorption of saccharide 12 to a certain degree is inevitable. If the target material is separated and purified by using the organic polymer particle 11 in which a saccharide is physically adsorbed, problems such as reduced utilization efficiency of the carboxyl group 14, an increase in nonspecific adsorption due to the surface of the particle 10 partially made porous, and detachment of the once-trapped target material together with the physically adsorbed saccharide during separation and purification operations may occur.

2-1-2. Second Step

In the second step of this embodiment, the saccharide physically adsorbed on the surface of the organic polymer particle 11 in the first step can be extracted by a basic solution by treating the organic polymer particle 11 of which the surface was covered by saccharide 12 with the basic solution. In the second step, by treating the organic polymer particle 11 with a sufficient amount of basic solution, only chemically bonded saccharide 12 finally remains on the surface of the organic polymer particle 11 (see FIG. 2), whereby the above-mentioned problems caused by the physically adsorbed saccharide can be overcome. The carrier polymer particles comprising organic polymer particle 11 and the saccharide 12 covering the surface of the organic polymer particle 11, from which physically adsorbed saccharide has been removed, can be obtained by the above steps.

The basic solution used here is not particularly limited insofar as the solution can extract the physically adsorbed saccharide. For example, alkaline aqueous solutions such as a sodium hydroxide aqueous solution, a potassium hydroxide aqueous solution, a lithium hydroxide aqueous solution, a sodium carbonate aqueous solution, a sodium hydrogen carbonate aqueous solution, a potassium carbonate aqueous solution, a potassium hydrogen carbonate aqueous solution, a lithium carbonate aqueous solution, ammonia water, and a hydroxyl tetramethylammonium aqueous solution; and aqueous solutions of water-soluble organic amines can be given.

The concentration of the basic aqueous solution used here is usually 0.001 M or more. The treating temperature is usually 0 to 50° C., and preferably 0 to 30° C.

Although inferior to the basic solution in respect of efficiency, the physically-adsorbed saccharide can also be extracted by treating with an appropriate electrolytic solution.

2-1-3. Third Step

The process for producing the carrier polymer particles may further comprise a step of chemically bonding the saccharide to a probe for specifically trapping a target material (a third step). The particles obtained by the third step have a probe to specifically trap a target material chemically bonded to a saccharide (such particles are herein referred to as "probe-bonded particles). Although not specifically limited, the saccharide and the probe may bond via a chemical bond such as an —O— bond, an —S— bond, an —SO— bond, an —$SO_2$— bond, a —CO— bond, a —$CO_2$— bond, an —$NR^1$— bond (wherein $R^1$ is an alkyl group or H), an —$N^+R^2R^3$— bond (wherein $R^2$ and $R^3$ are individually an alkyl group or H), an —NHCO— bond, or a —$PO_2$— bond. The saccharide and the probe can be chemically bonded by, for example, chemically reacting a functional group in the saccharide with a functional group in the probe.

The functional group in the saccharide and the functional group in the probe are not specifically limited. As examples, groups such as a hydroxyl group, an acyl group, a mercapto group, an amino group, an aminoacyl group, a carbonyl group, a formyl group, a carboxyl group, an amide group, a sulfonic group, a phosphate group, an epoxy group, a tosyl group, an azido group, a vinyl group, and an allyl group can be given.

In this embodiment, the term "target material" refers to a target to be trapped by the probe-bonded particles according to this embodiment. As an example of the target material, a biologically-related material can be given. In the embodiment, the term "biologically-related material" refers to all materials relating to biological bodies. As examples of the biologically-related material, materials contained in biological bodies, materials derived from materials contained in biological bodies, and materials which can be used in biological bodies can be given.

More specific examples of the biologically-related materials include, but are not limited to, proteins (such as an enzyme, an antibody, and an acceptor), peptides (such as glutathione and RGD peptides), nucleic acids (such as DNA and RNA), carbohydrates, lipids, and other cells and materials (such as various blood-originating materials and various floating cells containing various blood cells such as platelets, erythrocytes, and leukocytes).

When the probe is a protein, for example, the probe can be chemically bonded to the saccharide by, for example, reacting a functional group in the protein (for example, an amino group or a carboxyl group) with a functional group in the saccharide (for example, a carboxyl group, a hydroxyl group, or an amino group). In this instance, the probe and the saccharide can be bonded through an amide bond or an ester bond.

When the probe is a nucleic acid, for example, the probe can be chemically bonded to the saccharide by, for example, reacting a functional group in the nucleic acid (for example, a phosphoric acid group) with a functional group in the saccharide (for example, a hydroxyl group). In this instance, the probe and the saccharide can be bonded through a phosphodiester bond.

Although not particularly limited, the probe which can be used with the particles for specific trapping includes, for example, a protein (for example, an antibody, an antigen, an enzyme, an acceptor, and a hormone), a peptide, a nucleic acid (for example, DNA and RNA), a glycoside compound, and a synthetic chemical material (for example, a pharmaceutical candidate compound).

When the probe is an antibody (or an antigen), the target material may be an antigen (or an antibody) which specifically bonds to the antibody (or the antigen).

When the probe is a nucleic acid, the target material may be a nucleic acid which specifically bonds to the nucleic acid. When the probe is an enzyme, an acceptor, or a hormone, the target material may be a chemical compound which specifically bonds to the enzyme, the acceptor, or the hormone.

2-1-4. Materials Used for Producing Carrier Polymer Particles of this Embodiment Next, the materials used for producing the carrier polymer particles according to this embodiment are explained in detail.

2-1-4A. Organic Polymer Particles

The average particle diameter of the organic polymer particles used for producing the carrier polymer particles of this embodiment is 0.1 to 20 micrometers, more preferably 0.3 to 15 micrometers, and most preferably 1 to 10 micrometers. Also, the coefficient of variation of the organic polymer particles used in the embodiment is normally 30% or less, preferably 20% or less, and more preferably 10% or less.

In this embodiment, the organic polymer particles may be used as base particles of the carrier polymer particles produced according to this embodiment. Organic polymer particles are suitable as base particles, since it is easy to cover the surface of organic polymer particles with a saccharide which is bonded by chemical bonding. Also, magnetic particles may be used as the organic polymer particles.

As explained above, when the carrier polymer particles produced according to this embodiment are dispersed in a solvent, nonspecific adsorption of biologically-related materials such as proteins increases if the organic polymer particles are dispersed in a dispersion medium or the organic polymer particles swell by the solvent. For this reason, it is desirable that the organic polymer particles do not dissolve in the dispersion medium. An aqueous medium may be used as the dispersion medium, for example. The aqueous medium means water or a mixture of water and a solvent which dissolves in water (for example, alcohols and alkylene glycol derivatives).

As the organic polymer particles, polymers used for the organic polymer particles of the first embodiment can be used. In addition, the process described in the first embodiment can be used. Vinyl polymers are particularly preferable as the polymer constituting the organic polymer particles.

As the magnetic particles, those given as the magnetic particles in first embodiment may be used.

2-1-4B. Saccharide

As examples of the saccharide having a carboxyl group used for producing the carrier polymer particles according to this embodiment, saccharides obtained by chemically modifying at least a part of the functional groups (for example, a hydroxyl group and an amino group) in the molecule of a saccharide by introducing a carboxyl group, for example, carboxymethylcellulose, carboxymethyldextran, and polysaccharides originally possessing a carboxyl group (such as alginic acid and hyaluronic acid) can be given. Such a saccharide to be modified by introducing a carboxyl group includes furanoses such as fructose, arabinose, xylose, ribose, and deoxyribose; pyranoses such as glucose, mannose, and galactose; monosaccharides such as septanoses; disaccharides such as trehalose, lactose, kojibiose, nigerose, maltose, isomaltose, sophorose, laminaribiose, cellobiose, and gentiobiose; and polysaccharides such as starch, amylose, amylopectin, dextrin, glycogen, cyclodextrin, cellulose, agarose, inulin, glucomannan, chitin, and chitosan.

A general chemical reaction may be used for chemically modifying the saccharide to introduce a carboxylic group without any particular limitations. The chemical modification may be carried out in two or more stages as required. In order to cover the surface of organic polymer particles by the chemical bond of the organic polymer particles and the saccharides, a polysaccharide with a high molecular weight is preferable from the viewpoint of coating efficiency. Carboxymethylcellulose and carboxymethyldextran are particularly preferable as the saccharide having a carboxyl group.

2-1-5. Carrier Polymer Particles

The particle diameter of the carrier polymer particles produced by this embodiment is preferably 0.1 to 17 micrometers, and more preferably 1 to 10 micrometers. When the particle diameter is less than 0.1 micrometer, since separation using centrifugal separation or the like takes a long time and separation of the washing solvent such as water and the particles is insufficient, there are situations in which the removal of non-target molecules (for example, biologically-related materials such as proteins) is insufficient and thus, sufficient purification is not possible. In contrast, since particles with a diameter exceeding 17 micrometers reduces the surface area of the particles, there may be situations in which the trapped amount of the biologically-related material such as a protein, which is the target, is small.

After preparation according to the above-described process, the carrier polymer particles of this embodiment can be used as carrier particles after adjusting the pH and washing the surface by purification processing such as dialysis, ultrafiltration, and centrifugation, as required.

Although it is possible to use the carrier polymer particles produced by this embodiment as they are, they can also be used as a dispersion liquid in which the particles are dispersed in a dispersion medium in order to efficiently carry out a reaction with a compound. As a dispersion medium, those given as the dispersion medium in first embodiment may be used.

In addition, the carrier polymer particles of the embodiment may be probe-bonded particles in which a probe to specifically trap a target material chemically bonds to the saccharide. The probe may be chemically bonded to the saccharide by the above-described third step. The particle diameter of the probe-bonded particles is preferably from 0.1 to 20 micrometers, more preferably from 0.3 to 17 micrometers, and still more preferably from 0.5 to 10 micrometers.

2-2. Application

The carrier polymer particles produced by this embodiment may be used as chemical bonding carrier polymer particles in the drug discovery field and also as chemical bonding carrier polymer particles for diagnostic drugs.

More particularly, the carrier polymer particles produced by this embodiment can be used for selecting and purifying a target material (such as proteins) exhibiting specific interactions with a chemical compound to be analyzed by immobilizing the chemical compound to be analyzed by chemical bonding.

In addition, the carrier polymer particles produced by this embodiment can also be used as biologically-related material carrier polymer particles for sensing proteins such as an antibody, an antigen, an enzyme, and a hormone; nucleic acids such as DNA and RNA; and biologically-related glycoside compounds (hereinafter referred to collectively as "biologically-related material") on the surface of particles by a chemical bonding method.

The applications of the carrier polymer particles produced by this embodiment is not limited to the above-mentioned applications of chemical bonding carrier polymer particles in the drug discovery field and chemical bonding carrier polymer particles for diagnostic drugs. The carrier polymer particles can be used in a wide variety of fields such as biologically-related fields, paints, papers, electrophotography, cosmetics, medical supplies, agricultural chemicals, foods, and catalysts.

3. Third Embodiment 3-1. Magnetic Particles for Specific Trapping

The magnetic particles for specific trapping according to the third embodiment of the invention comprise magnetic particles and a saccharide. The saccharide may cover the surface of the magnetic particles.

The magnetic particles chemically bond with the saccharide in the magnetic particles for specific trapping. Although not specifically limited, the chemical bond of the magnetic particles and the saccharide is preferably based on a bonding group containing at least an amide bond or an ester bond.

In addition, a probe to specifically trap the target material chemically bonds with the saccharide in the magnetic particles for specific trapping of this embodiment. Although not specifically limited, the saccharide and the probe may bond via a chemical bond such as an —O— bond, an —S— bond, an —SO— bond, an —SO$_2$— bond, a —CO— bond, a —CO$_2$— bond, an —NR— bond (wherein R is an alkyl group or H), an —N$^+$R$^2$R$^3$— bond (wherein R$^2$ and R$^3$ are individually an alkyl group or H), an —NHCO— bond, or a —PO$_2$— bond. The saccharide and the probe can be chemically bonded by, for example, chemically reacting a functional group in the saccharide with a functional group in the probe.

The functional group in the saccharide and the functional group in the probe are not specifically limited. As examples, groups such as a hydroxyl group, an acyl group, a mercapto group, an amino group, an amino acyl group, a carbonyl group, a formyl group, a carboxyl group, an amide group, a sulfonic group, a phosphate group, an epoxy group, a tosyl group, an azido group, a vinyl group, and an allyl group can be given.

In this embodiment, the term "target material" refers to a target to be trapped by the magnetic particles for specific trapping according to this embodiment. As an example of the target material, a biologically related material can be given. In the embodiment, the term "biologically-related material" refers to all materials relating to biological bodies. As examples of the biologically-related material, materials contained in biological bodies, materials derived from materials contained in biological bodies, and materials which can be used in biological bodies can be given.

More specific examples of the biologically-related materials include, but are not limited to, proteins (e.g., enzymes, antibodies, and acceptors), peptides (e.g., glutathione, RGD peptides), nucleic acids (e.g., DNA and RNA), carbohydrates, lipids, and other cells and substances (e.g., various blood-originating substances and various floating cells containing various blood cells such as platelets, erythrocytes, and leukocytes).

When the probe is a protein, for example, the probe can be chemically bonded to a saccharide by, for example, reacting a functional group in the protein (for example, an amino group and a carboxyl group) with a functional group in the saccharide (for example, a carboxyl group, a hydroxyl group, and an amino group). In this instance, the probe and the saccharide can be bonded through an amide bond or an ester bond.

When the probe is a nucleic acid, for example, the probe can be chemically bonded to a saccharide by, for example, reacting a functional group in the nucleic acid (for example, a phosphoric acid group) with a functional group in the saccharide (for example, a hydroxyl group). In this instance, the probe and the saccharide can be bonded through a phosphodiester bond.

Although not particularly limited, the probe which can be used with the particles for specific trapping includes, for example, a protein (for example, an antibody, an antigen, an enzyme, an acceptor, and a hormone), a peptide, a nucleic acid (for example, DNA and RNA), a glycoside compound, and a synthetic chemical substance (for example, a pharmaceutical candidate compound).

When the probe is an antibody (or an antigen), the target material may be an antigen (or an antibody) which specifically bonds to the antibody (or the antigen).

When the probe is a nucleic acid, the target material may be a nucleic acid which specifically bonds to the nucleic acid. When the probe is an enzyme, an acceptor, or a hormone, the target material may be a chemical compound which specifically bonds to the enzyme, the acceptor, or the hormone.

Although the magnetic particles for specific trapping according to this embodiment can be used as they are, in order to efficiently perform a reaction with a compound, it is possible to use them dispersed in a dispersion medium. As a dispersion medium, those given as the dispersion medium in first embodiment may be used.

The particle diameter of the magnetic particles for specific trapping according to this embodiment is from 0.1 to 20 micrometers, preferably from 0.3 to 17 micrometers, and more preferably from 0.5 to 10 micrometers. If the particle diameter is less than 0.1 micrometer, it takes a long time for separation using magnetism or the like, resulting in insufficient separation of the particles from a washing solvent such as water. This makes it difficult to sufficiently remove materials other than the target material, giving rise to inadequate purification. On the other hand, if the particle diameter is more than 20 micrometers, the amount of the target material which can be trapped may be small due to the surface area becoming smaller.

Each of the components of the magnetic particles for specific trapping of this embodiment are described below.

3-1-1. Magnetic Particles

The average particle diameter of the nuclear particles used in this embodiment is preferably from 0.1 to 20 micrometers, more preferably from 0.3 to 17 micrometers, and still more preferably from 0.5 to 10 micrometers. If the particle diameter of the magnetic particles is less than 0.1 micrometer, it may take a long time for separation and purification using magnetism; and if more than 20 micrometers, the amount of trapped target material may be small due to the surface area becoming smaller.

As mentioned above, when the magnetic particles for specific trapping of this embodiment are dispersed in a solvent, the nonspecific adsorption of the target materials increases if the magnetic particles are dissolved in the dispersion medium or the magnetic particles are swollen by the solvent. For this reason, it is desirable that the magnetic particles are not dissolved in a solvent.

Although the internal composition of the magnetic particles used in this embodiment may be homogeneous, most magnetic materials making up the homogeneous magnetic particles with a particle diameter in the above-mentioned preferable range are paramagnetic. If repeatedly separated and refined by magnetism, the magnetic particles may lose their capability of being dispersed in dispersion media. For this reason, it is preferable that the magnetic particles of this embodiment have a heterogeneous internal composition containing fine particles of a magnetic material exhibiting small residual magnetization. As the inner structure of the magnetic particles having such a heterogeneous internal composition, (i) a structure in which the magnetic particles are dispersed in a continuous phase of a non-magnetic material such as a polymer, (ii) a structure consisting of a secondary aggregate of fine particles of a magnetic material as a core and a non-magnetic material such as a polymer layer as a shell, and (iii) a structure consisting of a non-magnetic material such as a polymer (non-magnetic nuclear particles) as a core and a magnetic material layer (secondary aggregate materials of fine particles of a magnetic material) of supermagnetic nanoparticles provided on the surface of the nuclear particles, and the like can be given. As the polymer which can be used as the core, polymers described later as the polymer forming the magnetic particles may be used. The fine particles of a magnetic material in the above structures (i) to (iii) are preferably fine particles of at least one of $Fe_2O_3$ and $Fe_3O_4$.

In the case of the structure of (iii) above, in which the inner structure consists of a core of a non-magnetic material such as a polymer (non-magnetic nuclear particles) and a shell of a magnetic material layer (a secondary aggregate of fine particles of a magnetic material), it is preferable that a polymer layer be further formed on the magnetic material layer. In this instance, the polymer layer may be formed by polymerization on the surface of the mother particles which contain nuclear particles (core) and a magnetic material layer (shell) formed on the surface of the nuclear particles. The magnetic material layer (shell) may contain fine particles of a magnetic material which contain at least one of $Fe_2O_3$ and $Fe_3O_4$. As the polymer which can be used for the polymer layer, polymers described later as the polymer forming the magnetic particles may be used.

In the case of the above structure (iii), the magnetic material layer may be produced by, for example, mixing the non-magnetic material nuclear particles with the fine particles of a magnetic material and causing the fine particles of a magnetic material to be physically adsorbed on the surface of the non-magnetic material nuclear particles. In this embodiment, "physical adsorption" refers to adsorption not involving a chemical reaction. As the principle of "physical adsorption", hydrophobic/hydrophobic adsorption, molten bonding or adsorption, fusion bonding or adsorption, hydrogen bonding, Van-der-Waals bonding, and the like can be given, for example.

The magnetic particles of the structure (iii) above can be obtained by, for example, suspension polymerization of the above vinyl monomer or polymer bulk shattering. For example, the magnetic particles can be obtained by the two-stage swelling polymerization method using seed particles described in JP-UM-B-57-24369, the polymerization method described in J. Polym. Sci., Polymer Letter Ed., 21, 937 (1963), and the methods described in JP-A-61-215602, JP-A-61-215603, and JP-A-61-215604.

The magnetic particles of the structure (iii) above can also be prepared by a method utilizing hydrophobic/hydrophobic adsorption. For example, a method selecting non-magnetic nuclear particles and fine particles of a magnetic material, each having a hydrophobic or hydrophobized surface, and dry-blending these non-magnetic nuclear particles and fine particles of a magnetic material, and a method sufficiently dispersing the non-magnetic nuclear particles and fine particles of a magnetic material in a solvent (such as toluene or hexane) with good dispersibility without damaging both particles, followed by vaporization of the solvent while mixing can be given.

Alternatively, in the case of the above structure (iii), the magnetic particles may be produced by physically applying a strong external force to cause the fine particles of a magnetic material to be adsorbed on the surface of the non-magnetic material nuclear particles. As examples of the method for physically applying a strong force, a method using a mortar, an automatic mortar, or a ball mill; a blade-pressuring type powder compressing method; a method utilizing a mechanochemical effect such as a mechanofusion method; and a method using an impact in a high-speed air stream such as a jet mill, a hybridizer, or the like can be given. In order to efficiently produce a firmly bound complex, a strong physical adsorption force is desirable. As the method, stirring using a vessel equipped with a stirrer at a peripheral velocity of stirring blades of preferably 15 m/sec or more, more preferably 30 m/sec or more, and still more preferably from 40 to 150 m/sec can be given. If the stirring blade peripheral velocity is less than 15 m/sec, sufficient energy for causing fine particles of a magnetic material to be adsorbed on the surface of non-magnetic nuclear particles may not be obtained. Although there are no specific limitations to the upper limit of the peripheral speed of the stirring blades, the upper limit of the peripheral speed is determined according to the apparatus to be used, energy efficiency, and the like.

As the polymer used for forming the magnetic particles of this embodiment, those mentioned in connection with the organic polymer particles of the first embodiment can be given.

3-1-2. Saccharide

As the saccharide used for forming the magnetic particles for specific trapping of this embodiment, those mentioned in the first embodiment can be given.

3-2. Process for Producing Magnetic Particles for Specific Trapping

The process for producing the magnetic particles for specific trapping according to this embodiment comprises chemically bonding magnetic particles with a diameter of 0.1 to 20 micrometers with a saccharide and chemically bonding a probe for specifically trapping the target material with a saccharide. The surface of the magnetic particles can be covered with a saccharide by chemically bonding the magnetic particles with the saccharide.

In this embodiment, a general chemical reaction may be used for chemically bonding the magnetic particles with the saccharide without any particular limitations. For example, the magnetic particles used for producing the magnetic particles for specific trapping according to this embodiment may have two or more functional groups (first functional groups) on the surface. The first functional group may be a functional group introduced when the particle shape of magnetic particles is formed or a functional group obtained by converting the functional group after the particle shape of magnetic particles has been formed. The conversion of functional groups may be carried out two or more times.

Although not particularly limited, when the functional group introduced when forming the particle shape of the magnetic particles is an epoxy group, an amino group produced by reacting the epoxy group with a large excess amount of ammonia or an appropriate diamine compound may be the first functional group, or when the functional group introduced when forming the particle shape of the magnetic particles is a hydroxyl group, for example, an amino group produced by converting the hydroxyl group into a tosyl group and reacting the tosyl group with a large excess amount of an appropriate diamine compound may be the first functional group. For example, in the magnetic particles Am-6 and Am-7 respectively obtained in the later-described Experimental Examples 8 and 9, the first functional group can be the amino group.

The saccharide used for producing the magnetic particles for specific trapping according to this embodiment may have two or more functional groups (second functional groups) in the molecule.

As the functional group which can be used as the first functional group and/or the second functional group, a carboxyl group, a hydroxyl group, an epoxy group, an amino group, a mercapto group, a vinyl group, an allyl group, an acrylic group, a methacryl group, a tosyl group, an azido group, and the like can be given. The first functional group and the second functional group are reactive with each other. Although not particularly limited, when the first functional group is an epoxy group, for example, the second functional group may be an amino group, or when the first functional group is an amino group, for example, the second functional group may be a carboxyl group.

It is possible to chemically bond the magnetic particles with the saccharide by reacting the first functional group and the second functional group, whereby the magnetic particles for specific trapping according to this embodiment can be obtained.

In this embodiment, a general chemical reaction may be used for chemically bonding the magnetic particles to the saccharide without any particular limitations. The probe and the saccharide can be chemically bonded by, for example, chemically reacting a functional group in the probe with a functional group in the saccharide. The functional group contained in the probe and the functional group contained in the saccharide are the groups mentioned above.

After preparation according to the above-described process, the magnetic particles for specific trapping of this embodiment can be used as carrier particles after adjusting the pH and washing the surface by purification processing such as dialysis, ultrafiltration, and centrifugation, as required.

4. Examples

The invention will now be described in more detail by way of examples, which should not be construed as limiting the invention. In the Examples, "%" and "part" are indicated on the weight basis.

4-1. Example 1
4-1-1. Evaluation Method
4-1-1A. Evaluation 1 of Nonspecific Adsorption (Protein Adsorption)
4-1-1A-1. Pre-Washing Step Carrier polymer particles prepared in the later-described Experimental Examples and Comparative Examples were diluted with and dispersed in purified water to obtain dispersion liquids, each having a particle concentration of 1 wt %. 500 microliters of the dispersion liquid was put into a microcentrifuge tube ("Safe-Lock Tube" manufactured by Eppendorf AG) and centrifuged (15,000 rpm, 15° C., 10 minutes) using a centrifugal separator ("MX-150" manufactured by Tomy Seiki Co.) to remove the supernatant liquid. 500 microliters of a PBS(−) buffer solution was added to the tube which contained the precipitate, and the mixture was vibrated by a touch mixer to disperse the particles.

4-1-1A-2. Protein Adsorption Reaction Step

Then, 500 microliters of a PBS(−) solution of 1 wt % BSA (bovine serum albumin) was added to the tube and the mixture was vibrated by a touch mixer to disperse the particles in the solution, followed by mixing by rotation and inversion for two hours at room temperature.

4-1-1A-3. Washing Step

After centrifugal separation, the supernatant liquid was removed. 1 ml of 10 mM HEPES was added to the tube and the particles were dispersed by vibration using a touch mixer. After repeating the same procedure twice, the content was transferred to another microcentrifuge tube to perform centrifugal separation, and the supernatant liquid was removed.

4-1-1A-4. Detaching Step

After the addition of 50 microliters of a 0.5% aqueous solution of SDS (sodium dodecylsulfate), the mixture was gently vibrated by a touch mixer to disperse the particles. After allowing the mixture to stand for 10 minutes, centrifugal separation was performed and 20 microliters of the supernatant liquid was collected.

4-1-1A-5. Sampling Step 2-mercaptoethanol was dissolved in a premix sample buffer solution manufactured by Bio-Rad Laboratories, Inc. to a concentration of 2 wt % (this solution is hereinafter referred to as "sample buffer"). 20 microliters of the solution was collected in the microcentrifuge tube. 20 microliters of the supernatant liquid collected in the above step was mixed and heated at 100° C. for five minutes in a tube heater.

As controls, a 1 wt % BSA solution in PBS(−) was diluted with a 2% SDS solution to 5,000 fold, 10,000 fold, and 20,000 fold. 20 microliters of each of the diluted solutions was mixed with 20 microliters of the sample buffer and heated in a tube heated at 100° C. for five minutes. The resulting solutions are called "reference diluted BSA".

4-1-1A-6. Electrophoresis (SDS-PAGE)

The reference diluted BSA was applied to a vertical electrophoresis system ("Mini-PROTEAN3" manufactured by Bio-Rad Laboratories, Inc.) in an amount of 20 microliters per one lane of the gel to perform electrophoresis using a precast polyacrylamide gel ("Ready Gel J" (15%) manufactured by Bio-Rad Laboratories, Inc.) and a premix electrophoresis buffer solution manufactured by Bio-Rad Laboratories, Inc. The gel was stained by a standard staining method using "Silver Stain Plus Kit" manufactured by Bio-Rad Laboratories, Inc. An image was produced by scanning the stained gel using a densitometer "GS-700" manufactured by Bio-Rad Laboratories, Inc. and the product of the concentration and the area of the BSA band in the gel was determined using an analysis software "Multi-Analyst".

Since the weight of BSA which flows per one lane of the gel is known in the reference dilution BSA, a calibration curve was drawn from the product of the band concentration and the area, and the amount of BSA detached from the particles was converted on a weight basis based on the calibration curve. The resulting weight corresponded to the amount of BSA which had been adsorbed per 1 mg of the particles.

4-1-1B. Particle Diameter

The diameter of the particles with a diameter of 1 micrometer or more was measured using a laser diffraction particle size distribution analyzer ("SALD-200V" manufactured by Shimadzu Corp.) and the diameter of the particles with a diameter of less than 1 micrometer was measured using a particle size distribution analyzer based on a laser dispersion diffraction method ("LS 13 320" manufactured by Beckmann Coulter).

4-1-1C Infrared Absorption Spectrum

The infrared absorption spectrum was measured by a KBr method using a Fourier-transform infrared spectrophotometer ("JIR-5500" manufactured by JEOL Ltd.).

4-1-2. Synthesis Examples 4-1-2A. Synthesis Example 1 (Synthesis of Organic Polymer Particles A-1)

The organic polymer particles A-1 were prepared by a two-step swelling polymerization method using seed particles.

Using polystyrene particles with a particle diameter of 0.98 micrometers obtained by soap-free polymerization as seed particles, a water dispersion (solid content: 5.0 g) was prepared by dispersing these polystyrene particles in 500 g of water in a nitrogen atmosphere. According to the two step swelling polymerization method (based on the method described in JP-B-57-24369), an organic solvent (0.1 g of "Shellsol TK") was added to the seed particles as a first step and monomers (70 g of MMA (methyl methacrylate), 10 g of TMP (trimethylolpropane trimethacrylate), and 20 g of GMA (glycidyl methacrylate)) were added as a second step to cause them to be adsorbed. Then, 2 g of AIBN (azobisisobutyronitrile) was added and the mixture was slowly stirred at 75° C. for 24 hours. The reaction solution was cooled and filtered through a 500 mesh wire gauze to confirm that 99% of the product passed through the wire gauze. The polymerization stability was good. The polymerization yield was 99%. The particle diameter of the resulting organic polymer particles A-1 was 2.71 micrometers, the coefficient of variation of the particle diameter was 2%, and the particles were monodisperse particles.

4-1-2B. Synthesis Example 2 (Synthesis of Organic Polymer Particles A-2)

Organic polymer particles A-2 with a particle diameter of 2.64 micrometers and a coefficient of variation of 2% were obtained in the same manner as in Synthetic Example 1, except for using 50 g of MMA, 10 g of TMP, and 40 g of GMA as monomers.

4-1-2C. Synthesis Example 3 (Synthesis of Organic Polymer Particles A-3)

Organic polymer particles A-3 with a particle diameter of 2.61 micrometers and a coefficient of variation of 2.1% were obtained in the same manner as in Synthetic Example 1, except for using 30 g of MMA, 10 g of TMP, and 60 g of GMA as monomers.

4-1-2D. Synthesis Example 4 (Synthesis of Organic Polymer Particles A-4)

Organic polymer particles A-4 with a particle diameter of 7.05 micrometers and a coefficient of variation of 2.3% were obtained in the same manner as in Synthetic Example 3, except for using polystyrene particles with a particle diameter of 2.6 micrometers as seed particles.

4-1-2E. Synthesis Example 5 (Synthesis of Organic Polymer Particles A-5)

Organic polymer particles A-5 with a particle diameter of 2.58 micrometers and a coefficient of variation of 2.3% were obtained in the same manner as in Synthetic Example 1, except for using 10 g of TMP and 90 g of GMA as monomers.

4-1-2F. Synthesis Example 6 (Synthesis of Saccharide CMC-1)

Diluted hydrochloric acid was added to an aqueous solution of carboxymethylcellulose sodium salt ("APP-84" manufactured by Nippon Paper Chemicals Co., Ltd., a compound having an average molecular weight of 17,000 and an average of 0.7 carboxyl groups per one glucose unit) until the solution has a pH of 2 or less. The resulting solution was dialyzed and concentrated to obtain a 2.5% aqueous solution of carboxymethylcellulose CMC-1.

4-1-2G Synthesis Example 7 (Synthesis of Saccharide CMD-1)

0.72 g of sodium hydroxide and 1.04 g of bromoacetic acid were added to 2.5 g of a 10 wt % aqueous solution of Dextran T500 (average molecular weight: 500,000) manufactured by Pharmacia AB, and the mixture was stirred for several minutes until homogenized. The solution was maintained at 40° C. for 60 hours and then cooled with ice. After the addition of diluted hydrochloric acid to make the pH 2 or less, the solution was dialyzed and freeze-dried to obtain carboxymethyldextran CMD-1. Carboxylic acid contained in CMD-1 was measured by titration to find that CMD-1 contained an average of 0.4 carboxylic acid groups per one glucose unit.

4-1-3. Experimental Example 1

The polymer particles isolated from the dispersion liquid of organic polymer particles A-1 by centrifugation were washed by dispersing in acetone, followed by centrifugation. This washing procedure was repeated three times. The resulting particles were dried. 0.50 g of the particles was put into a 100 ml flask and 25 g of ethylenediamine was added. The particles were irradiated with indirect ultrasonic radiation for 10 minutes and dispersed. The dispersion liquid was stirred at 50° C. in a nitrogen atmosphere for six hours, followed by isolation of the particles by centrifugal separation. The particles were washed twice with methanol and three times with a 3:1 (by volume) mixture of water and methanol, and dried to obtain 0.54 g of organic polymer particles Am-1 as a white powder.

The weight of the organic polymer particles Am-1 was larger than the weight of the organic polymer particles A-1. Comparison of the infrared absorption spectrum of the organic polymer particles Am-1 (after ethylenediamine treatment) with the infrared absorption spectrum of the organic polymer particles A-1 (before ethylenediamine treatment) indicates that in the infrared absorption spectrum of the organic polymer particles Am-1, a peak originating from an epoxy group, which was observed around 900 $cm^{-1}$ of the infrared absorption spectrum of the organic polymer particles A-1, disappeared and, instead, peaks typical to a primary amine appeared around 3,300 $cm^{-1}$ and 3,500 $cm^{-1}$. The organic polymer particles Am-1 were thus confirmed to have an amino group introduced into the organic polymer particles A-1. That is, in the organic polymer particles Am-1, the first functional group 13 is an amino group.

30.6 mg of the organic polymer particles Am-1 was added to 1.2 g of a 2.5% aqueous solution of CMC-1 which was obtained in Synthetic Example 6. The mixture was irradiated with indirect supersonic waves for 30 minutes to disperse the polymer particles in the solution. Next, the dispersion liquid was cooled with ice, and 0.30 g of a 10 wt % aqueous solution of 1-ethyl-3-(3-dimethylaminopropyl)carbodiimide hydrochloride was added. The mixture was stirred under ice cooling for 12 hours. The particles were isolated by centrifugal separation, dispersed in purified water, isolated by centrifugal separation, and washed. This procedure was repeated 10 times, followed by drying to obtain 33.6 mg of carrier polymer particles P-1.

In addition to the peaks originating from the organic polymer particles Am-1 before the reaction, peaks originating from carboxymethylcellulose were observed around 3,400 cm$^{-1}$ and 1,600 cm$^{-1}$ in the infrared absorption spectrum of the carrier polymer particles P-1. The carrier polymer particles P-1 were thus confirmed to have a saccharide (carboxymethylcellulose) bonded to the organic polymer particles Am-1.

The nonspecific protein adsorption of the carrier polymer particles P-1 was measured according the above-described method to confirm that the value was very low (0.08 ng/mg).

4-1-4. Experimental Example 2

0.57 g of organic polymer particles Am-2 were obtained in the same manner as in Experimental Example 1, except for using a dispersion liquid of organic polymer particles A-2. Next, 34.0 mg of carboxymethylcellulose-bonded particles (carrier polymer particles) P-2 was obtained in the same manner as in Experimental Example 1, except for using the organic polymer particles Am-2 (29.6 mg) and a 2.5% aqueous solution of CMC-1 (1.2 g).

The nonspecific protein adsorption of the carrier polymer particles P-2 was measured according the above-described evaluation method to confirm that the value was very low (0.05 ng/mg).

4-1-5. Experimental Example 3

0.61 g of organic polymer particles Am-3 was obtained in the same manner as in Experimental Example 1, except for using a dispersion liquid of the organic polymer particles A-3. 36.2 mg of carboxymethylcellulose-bonded particles (carrier polymer particles) P-3 was obtained in the same manner as in Experimental Example 1, except for using the organic polymer particles Am-3 (29.9 mg) and a 2.5% aqueous solution of CMC-1 (1.2 g).

The nonspecific protein adsorption of the carrier polymer particles P-3 was measured according the above-described method to confirm that the value was very low (0.02 ng/mg).

4-1-6. Experimental Example 4

150 mg of CMD-1 which was obtained in Synthetic Example 7 was dissolved in 6 g of purified water. 150.5 mg of the organic polymer particles Am-1 which were obtained in Experimental Example 1 was added to the solution, and the mixture was irradiated with indirect supersonic waves for 30 minutes to disperse the particles in the solution. Next, the dispersion liquid was cooled with ice, and 1.40 g of a 5 wt % aqueous solution of 1-ethyl-3-(3-dimethylaminopropyl)carbodiimide hydrochloride was added. The mixture was stirred under ice cooling for 12 hours. The particles were isolated by centrifugal separation, dispersed in purified water, isolated by centrifugal separation, and washed. This procedure was repeated 10 times to obtain 156.2 mg of carrier polymer particles P-4.

In addition to the peaks originating from the organic polymer particles Am-1 before the reaction, peaks originating from carboxymethyldextran were observed around 3,400 cm$^{-1}$ and 1,600 cm$^{-1}$ in the infrared absorption spectrum of the carrier polymer particles P-4. The carrier polymer particles P-4 were thus confirmed to have a saccharide (carboxymethyldextran) bonded to the organic polymer particles Am-1.

The nonspecific protein adsorption of the carrier polymer particles P-4 was measured according the above-described evaluation method to confirm that the value was very low (0.07 ng/mg).

4-1-7. Experimental Example 5

0.62 g of organic polymer particles Am-4 was obtained in the same manner as in Experimental Example 1, except for using a dispersion liquid of the organic polymer particles A-4. 36.1 mg of carboxymethylcellulose-bonded particles (carrier polymer particles) P-5 was obtained in the same manner as in Experimental Example 1, except for using the organic polymer particles Am-4 (29.9 mg) and a 2.5% aqueous solution of CMC-1 (1.2 g).

The nonspecific protein adsorption of the carrier polymer particles P-5 was measured according the above-described evaluation method to confirm that the value was very low (0.05 ng/mg).

4-1-8. Experimental Example 6

The polymer particles isolated from the dispersion liquid of organic polymer particles A-5 by centrifugation were washed by dispersing in acetone, followed by centrifugation. This washing procedure was repeated three times. The resulting particles were dried.

0.50 g of the particles was put into a 100 ml flask and 46.5 g of dimethylsulfoxide was added. The mixture was irradiated with indirect ultrasonic radiation for 10 minutes and, after the addition of 3.5 g of a 10 wt % ethylenediamine solution (solvent: dimethylsulfoxide), the mixture was stirred at 50° C. in a nitrogen atmosphere for four hours, followed by isolation of the particles by centrifugal separation. The particles were washed twice with methanol and three times with a 3:1 (by volume) mixture of water and methanol, and dried to obtain 0.55 g of organic polymer particles Am-5 as a white powder.

The weight of the organic polymer particles Am-5 was larger than the weight of the organic polymer particles A-5. Comparison of the infrared absorption spectrum of the organic polymer particles Am-5 (after ethylenediamine treatment) with the infrared absorption spectrum of the organic polymer particles A-5 (before ethylenediamine treatment) indicates that in the infrared absorption spectrum of the organic polymer particles Am-5, a peak originating from an epoxy group, which was observed around 900 cm$^{-1}$ of the infrared absorption spectrum of the organic polymer particles A-5, disappeared and, instead, peaks typical to a primary amine appeared around 3,300 cm$^{-1}$ and 3,500 cm$^{-1}$. Based on the results, the organic polymer particles Am-5 were confirmed to have an amino group introduced into the organic polymer particles A-5. Based on the change in the peak intensity originating from the epoxy group before and after the treatment with ethylenediamine, the reaction rate of the epoxy group which exists in the organic polymer particles A-5 was presumed to be about 30%.

100 mg of the organic polymer particles Am-5 was added to a mixture of 15 g of 1 wt % sulfuric acid and 1.5 g of acetone. The mixture was irradiated with indirect ultrasonic radiation for 10 minutes and dispersed. The dispersion liquid was stirred at 50° C. for nine hours, followed by isolation of the particles by centrifugal separation.

The particles were washed three times with water, once with a 0.01 N sodium hydroxide aqueous solution, and five times with water, and dried to obtain 102 mg of particles.

Comparison of the infrared absorption spectrum of the organic polymer particles Am-5 before reaction with the infrared absorption spectrum of the particles obtained here (after the treatment with sulfuric acid) indicates that in the infrared absorption spectrum of the organic polymer particles Am-5, intensity of a peak originating from an epoxy group, which was observed around 900 cm$^{-1}$ of the infrared absorption spectrum of the organic polymer particles Am-5, disappeared and, instead, a peak originating from a hydroxyl group around 3,500 cm$^{-1}$ was intensified. Based on the results, it was confirmed that the epoxy group in the organic polymer particles Am-5 has been hydrolyzed.

33.1 mg of carboxymethylcellulose-bonded particles (carrier polymer particles) P-6 was obtained in the same manner as in Experimental Example 1, except for using 30.3 mg of the particles obtained above.

The nonspecific protein adsorption of the carrier polymer particles P-6 was measured according the above-described method to confirm that the value was less than the detectable limit (0.01 ng/mg).

4-1-9. Experimental Example 7

Sodium salt of carboxymethylcellulose ("APP-84" manufactured by Nippon Paper Industries Chemical, Inc.) was purified by dialyzing an aqueous solution, followed by freeze-drying. An experiment was carried out in the same manner as in Experimental Example 1, except for using the purified APP-84 (33 mg) and the organic polymer particles Am-7 (29.8 mg). Next, the particles were isolated by centrifugal separation, dispersed in purified water, and washed. This procedure was carried out five times, a procedure of dispersing the particles in a 0.01 N hydrochloric acid solution was carried out three times, and a procedure of dispersing in purified water, followed by centrifugal separation was carried out five times. The resulting particles were dried to obtain 33.7 mg of carboxymethylcellulose-bonded particles (carrier polymer particles) P-7.

The nonspecific protein adsorption of the carrier polymer particles P-7 was measured according the above-described evaluation method to confirm that the value was very low (0.05 ng/mg).

4-1-10. Comparative Example 1

The nonspecific protein adsorption of the organic polymer particles A-1 was measured according the above-described method to confirm that the value was high (1.3 ng/mg).

4-1-11. Comparative Example 2

Commercially available standard polystyrene particles ("STADEX SC200S" manufactured by JSR Corporation) was sufficiently washed with purified water and their nonspecific protein adsorption was measured according the above-described method to confirm that the value was very high (20 ng/mg).

4-1-12. Comparative Example 3

Particles of which the surface was covered with polyethylene glycol were obtained in the same manner as in Experimental Example 1, except for using a 2.5% aqueous solution of polyethylene glycol with both terminals modified with carboxylic acid (the number of average repetition of ethylene oxide unit: 10) instead of a 2.5% aqueous solution of CMC-1. The nonspecific protein adsorption of P-8 was measured according the above-described method to confirm that the value was 0.3 ng/mg.

4-2. Example 2

4-2-1. Method of Evaluation of Properties 4-2-1A. Particle Diameter

The diameter of the particles with a diameter of 1 micrometer or more was measured using a laser diffraction particle size distribution analyzer ("SALD-200V" manufactured by Shimadzu Corp.) and the diameter of the particles with a diameter of less than 1 micrometer was measured using a particle size distribution analyzer based on a laser dispersion diffraction method ("LS 13 320" manufactured by Beckmann Coulter).

4-2-1B Infrared Absorption Spectrum

The infrared absorption spectrum was measured by a KBr method using a Fourier-transform infrared spectrophotometer ("JIR-5500" manufactured by JEOL Ltd.).

4-2-2. Synthesis Examples 4-2-2A. Synthesis Example 8 (Synthesis of Magnetic Particles A-6)

Referring to the polymerization method described in JP-A-7-238105, styrene/divinylbenzene (96/4) copolymer particles (average particle diameter: 1.5 micrometers) were prepared. After polymerization, the particles were separated by centrifugation, washed with water, dried, and ground. The ground particles were used as core particles (a-1) (preparation of core particles).

Next, ferrite-type fine particles of a magnetic material (average primary particle diameter: 0.02 micrometers) with a hydrophobized surface were prepared by adding acetone to an oily magnetic fluid ("EXP series" manufactured by Ferrotec Corp.) to obtain a precipitate of the particles and drying the precipitate.

Then, 15 g of the above core particles (a-1) and 15 g of the hydrophobized fine particles of a magnetic material were thoroughly mixed in a mixer. The mixture was processed by a hybridization system ("NHS-O type" manufactured by Nara Machinery Co., Ltd.) at a peripheral blade (stirring blades) speed of 100 m/sec (16,200 rpm) for five minutes to obtain particles (1) with a magnetic material layer of fine particles of a magnetic material (M–1) with a number average particle diameter of 2.0 micrometers on the surface (preparation of magnetic material layer).

A 500 ml separable flask was charged with 375 g of an aqueous solution containing 0.25 wt % of sodium dodecylbenzenesulfonate and 0.25 wt % of a nonionic emulsifying agent ("Emulgen 150" manufactured by Kao Corp.), followed by the addition of 15 g of the above particles (1) having a magnetic material layer on the surface. After dispersion using a homogenizer, the resulting dispersion liquid was heated to 60° C. Next, a pre-emulsion, prepared by dispersing 27 g of MMA (methyl methacrylate), 3 g of TMP (trimethylolpropane trimethacrylate), and 0.6 g of di(3,5,5-trimethylhexanoyl) peroxide ("Peroyl 355" manufactured by NOF Corp.) in 150 g of an aqueous solution containing 0.25 wt % of sodium dodecylbenzenesulfonate and 0.25 wt % of a nonionic emulsifying agent ("Emulgen 150" manufactured by Kao Corp.), was dripped into the above 500 ml separable flask controlled at 60° C. over one and a half hours (a first stage polymerization for polymer layer formation).

After completing the dripping, the mixture was maintained at 60° C. while stirring for one hour. Next, a pre-emulsion, prepared by dispersing 7.5 g of MMA, 6 g of GMA (glycidyl methacrylate), 1.5 g of TMP, and 0.3 g of di(3,5,5-trimethylhexanoyl) peroxide ("Peroyl 355" manufactured by NOF Corp.) in 75 g of an aqueous solution containing 0.25 wt % of sodium dodecylbenzenesulfonate and 0.25 wt % of a nonionic emulsifying agent ("Emulgen 150" manufactured by Kao Corp.), was dripped to the above 500 ml separable flask controlled at 60° C. over one and a half hours (a second stage polymerization for polymer layer formation). After heating to 75° C., the polymerization was continued for a further two hours before completing the reaction. The resulting water dispersion of polymer-covered magnetic particles was purified by magnetism and gravity precipitation to obtain a water dispersion of magnetic particles A-6 with a solid component concentration of 1%. The number average particle diameter of the magnetic particles A-6 was 2.9 micrometers.

4-2-2B. Synthesis Example 9 (Synthesis of Magnetic Particles A-7)

A 500 ml separable flask was charged with 225 g of a 0.5 wt % sodium dodecylbenzenesulfonate aqueous solution. 9 g of the particles (1) having a magnetic material layer were added and dispersed using a homogenizer, and the resulting dispersion liquid was heated to 60° C. A pre-emulsion, prepared by dispersing 16.2 g of MMA, 1.8 g of TMP, and 0.36 g of di(3,5,5-trimethylhexanoyl)peroxide ("Peroyl 355" manufactured by NOF Corp.) in 90 g of an aqueous solution containing 0.5 wt % of sodium dodecylbenzenesulfonate was dripped into the above 500 ml separable flask controlled at 60° C. over one and a half hours (a first stage polymerization for polymer layer formation).

After completion of dripping, the mixture was maintained at 60° C. for one hour while stirring. A pre-emulsion, prepared by dispersing 8.1 g of GMA, 0.9 g of TMP, and 0.18 g of di(3,5,5-trimethylhexanoyl)peroxide ("Peroyl 355" manufactured by NOF Corp.) in 45 g of an aqueous solution containing 0.5 wt % of sodium dodecylbenzenesulfonate was dripped into the above 500 ml separable flask controlled at 60° C. over one and a half hours (a second stage polymerization for polymer layer formation). After heating to 75° C., the polymerization was continued for two hours before completing the reaction. The resulting water dispersion of polymer-covered magnetic particles was purified by magnetism and gravity precipitation to obtain a water dispersion of magnetic particles A-7 with a solid component concentration of 1%. The number average particle diameter of the magnetic particles A-7 was 2.6 micrometers.

4-2-2C. Synthesis Example 10 (Synthesis of Saccharide CMC-1)

Diluted hydrochloric acid was added to an aqueous solution of carboxymethylcellulose sodium salt ("APP-84" manufactured by Nippon Paper Chemicals Co., Ltd., a compound having an average molecular weight of 17,000 and an average of 0.7 carboxyl groups per one glucose unit) until the solution has a pH of 2 or less. The resulting solution was dialyzed and concentrated to obtain a 1% aqueous solution of a carboxymethylcellulose CMC-1.

4-2-2D. Synthesis Example 11 (Synthesis of Saccharide CMD-1)

0.72 g of sodium hydroxide and 1.04 g of bromoacetic acid were added to 2.5 g of a 10 wt % aqueous solution of Dextran T500 (average molecular weight: 500,000) manufactured by Pharmacia AB, and the mixture was stirred for several minutes to homogenize. The solution was maintained at 40° C. for 60 hours and then cooled with ice. After the addition of diluted hydrochloric acid to make the pH 2 or less, the solution was dialyzed and freeze-dried to obtain a carboxymethyldextran CMD-1. Carboxylic acid contained in CMD-1 was measured by titration to find that CMD-1 contained an average of 0.4 carboxylic acid groups per one glucose unit.

4-2-3. Experimental Example 8

4-2-3A. Preparation of Carrier Polymer Particles

Particles isolated from the water dispersion of magnetic particles A-6 obtained in Synthetic Example 8 by centrifugal separation were dispersed in acetone. After repeating a procedure of separating the particles by magnetism and washing five times, the particles were again dispersed in acetone and the supernatant liquid was removed by centrifugal separation. The particles obtained were dried. 0.50 g of the particles was put into a 100 ml flask and 25 g of ethylenediamine was added. Particles were irradiated with indirect ultrasonic radiation for 20 minutes and dispersed. The dispersion liquid was stirred at 50° C. in a nitrogen atmosphere for six hours, followed by isolation of the particles by centrifugal separation. The particles were washed five times with methanol and dried to obtain 0.49 g of aminated particles Am-6 as a brown powder. Comparison of the infrared absorption spectrum of the aminated particles Am-6 (after ethylenediamine treatment) with the infrared absorption spectrum of the magnetic particles A-6 (before ethylenediamine treatment) indicates that peaks typical to a primary amine appeared around 3,300 $cm^{-1}$ and 3,400 $cm^{-1}$ in the infrared absorption spectrum of the aminated particles Am-6. The aminated particles Am-6 were thus confirmed to have an amino group introduced into the magnetic organic polymer particles A-6.

150 mg of the aminated particles Am-6 was added to 3.75 g of a 1% aqueous solution of CMC-1 which was obtained in Synthetic Example 10. The dispersion liquid was irradiated with indirect supersonic waves for 20 minutes while cooling with ice. Next, 25.05 mg of 1-ethyl-3-(3-dimethylaminopropyl)carbodiimide hydrochloride was added to the dispersion liquid and the mixture was stirred under ice cooling for 20 hours. The particles were isolated by magnetic separation and dispersed in purified water. A procedure of magnetic separation and washing by dispersing in purified water was repeated five times. The resulting particles were again dispersed in purified water and centrifuged to remove the supernatant liquid, followed by drying to obtain 147 mg of carrier polymer particles P-9.

4-2-3B. Preparation of Probe-Bonded Polymer Particles

The carrier polymer particles obtained in Experimental Example 8 were diluted with and dispersed in purified water to obtain a water dispersion with a particle concentration of 1 wt %. 500 microliters of the dispersion liquid was put into a microcentrifuge tube ("Safe-Lock tube" manufactured by Eppendorf) and magnetically centrifuged using a magnetic stand ("Magical Trapper" manufactured by Toyobo Co., Ltd.) to remove the supernatant liquid. After washing three times with a 50 mM MES-NaOH buffer solution (pH 6, hereinafter referred to as "Buffer-1"), 0.8 mg of N-hydroxysuccinic acid imide (NHS) and 0.88 mg of 1-ethyl-3-(3-dimethylaminopropyl)carbodiimide (EDC) were added and stirred. Then, 0.05 mg of a protein (anti-alpha-fetoprotein antibody) which acts as a probe for specifically trapping the target material (alpha-fetoprotein, hereinafter referred to from time to time as "AFP") was added and the mixture was stirred at room temperature for two hours. After the reaction, the particles were separated by magnetic separation and the supernatant liquid was removed. Then, 500 microliters of a PBS (−) buffer solution containing 1% ethanol amine was added and the mixture was stirred at room temperature for two hours. Furthermore, after washing five times with a PBS (−) buffer solution, the particles were dispersed in 500 microliters of PBS (−) buffer solution to obtain a dispersion liquid of probe (antibody)-bonded particles.

4-2-3C. Evaluation of Specific Trapping Property

The specific trapping property of the probe-bonded particles obtained in this Experimental Example was evaluated according to the following method.

4-2-3C-1. Target Material (Protein) Adsorption Reaction Step 100 microliters of the above dispersion liquid of the probe-bonded particles was sampled in a separate tube. Particles were magnetically separated to remove the supernatant liquid. 500 microliters of a human blood serum solution containing 200 ng/ml of protein (human alpha-fetoprotein (AFP)) which is the target material was added to the particles. The mixture was vibrated by a touch mixer to disperse the particles in the solution, followed by mixing by rotation and inversion for two hours at room temperature.

4-2-3C-2. Washing Step

After magnetic separation, the supernatant liquid was removed. 1 ml of 10 mM HEPES was added to the tube and the particles were dispersed using a touch mixer. After further repeating the same procedure twice, the content was transferred to a new microcentrifuge tube to perform magnetic separation, and the supernatant liquid was removed.

4-2-3C-3. Detaching Step

After the addition of 50 microliters of a 0.5% aqueous solution of SDS (sodium dodecylsulfate), the mixture was gently vibrated to disperse the particles. After allowing the mixture to stand for 10 minutes, magnetic separation was performed and 20 microliters of the supernatant liquid was collected.

4-2-3C-4. Electrophoresis (SDS-PAGE)

2-mercaptoethanol was dissolved in a premix sample buffer solution manufactured by Bio-Rad Laboratories, Inc. to a concentration of 2 wt % (this solution is hereinafter referred to as "sample buffer"). 20 microliters of the solution was collected in a microcentrifuge tube. 20 microliters of the supernatant liquid collected in the above step was mixed and heated at 100° C. for five minutes in a tube heater.

As controls, a 1 mg/ml AFP/BSA (−) solution was diluted with an SDS solution to 100 fold, 200 fold, and 500 fold. 20 microliters of each of the diluted solutions were mixed with 20 microliters of the sample buffer and heated by a block heater at 100° C. for five minutes. The resulting solutions are called reference AFP dilutions.

The reference AFP dilutions were applied to a vertical electrophoresis system ("Mini-PROTEAN3" manufactured by Bio-Rad Laboratories, Inc.) in an amount of 20 microliters per one lane to perform electrophoresis using a precast polyacrylamide gel ("Ready Gel J" (15%) manufactured by Bio-Rad Laboratories, Inc.) and a premix electrophoresis buffer solution manufactured by Bio-Rad Laboratories, Inc. The gel was stained by a standard staining method using "Silver Stain Plus Kit" manufactured by Bio-Rad Laboratories, Inc. The stained gel was scanned using a densitometer "GS-700" manufactured by Bio-Rad Laboratories, Inc. to produce an image. The product of the concentration and the area of the AFP band in the gel were determined using an analysis software "Multi-Analyst".

Since the weight of AFP which flows per one lane of the gel is known in the reference dilution AFP, a calibration curve was drawn from the product of the concentration and the area of the band, and the amount of AFP detached from the particles was converted on a weight basis based on the calibration curve. The resulting weight corresponded to the amount of AFP which had been adsorbed per 0.2 mg of the particles.

4-2-4. Experimental Example 9
4-2-4A. Preparation of Carrier Polymer Particles 0.48 g of aminated particles Am-7 were obtained in the same manner as in Experimental Example 8, except for using the magnetic particles A-7. CMD-1 (150 mg) which was obtained in Synthetic Example 11 was dissolved in 6 g of purified water and 150.5 mg of the aminated particles Am-7 was added and dispersed in the solution by irradiation of indirect supersonic waves for 20 minutes. Next, the dispersion liquid was cooled with ice, and 1.40 g of a 5 wt % aqueous solution of 1-ethyl-3-(3-dimethylaminopropyl) carbodiimide hydrochloride was added. The mixture was stirred under ice cooling for 12 hours. The particles were isolated by magnetic separation and dispersed in purified water. A procedure of magnetic separation and washing by dispersing in purified water was repeated five times. The resulting particles were again dispersed in purified water and centrifuged to remove the supernatant liquid, followed by drying to obtain 147 mg of carrier polymer particles P-10.

4-2-4B. Preparation of Probe-Bonded Polymer Particles and Evaluation of Specific Trapping Property Probe(antibody)-bonded particles were obtained in the same manner as in Experimental Example 8 by using the carrier polymer particles P-10 obtained in this Experimental Example. The specific trapping property of the probe-bonded particles was evaluated according to the same method as in Experimental Example 8.

4-2-5. Comparative Example 4

Probe-bonded particles were obtained in the same manner as in Experimental Example 8 by using magnetic particles "MAG2101" manufactured by JSR Corporation. The specific trapping property of the probe-bonded particles was evaluated according to the same method as in Experimental Example 8. The surface of the magnetic particles used in the Comparative Example 4 was not covered with a saccharide.

4-2-6. Evaluation Result of Specific Trapping Property

Figure 3:
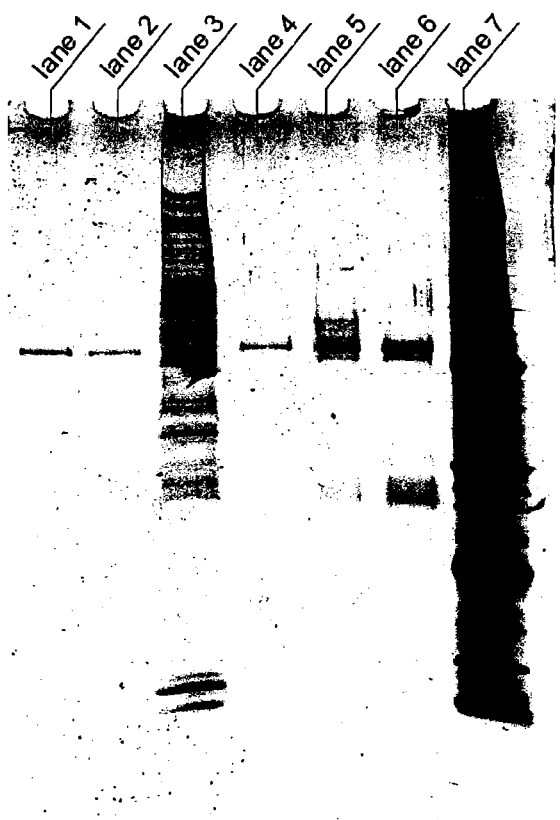
FIG. 3 is a photograph showing the specific trapping evaluation results of the probe-bonded particles obtained in Experimental Examples 8 and 9, and Comparative Example 4 (electrophoresis pattern of the proteins adsorbed on the probe bonding particles).

FIG. 3 is a photograph showing the evaluation results of the specific trapping property (an electrophoresis pattern of proteins adsorbed on the probe-bonded particles) obtained in Experimental Examples 8 and 9 and Comparative Example 4.

In FIG. 3, lane 1 indicates proteins trapped by the probe-bonded particles which were prepared by using the carrier polymer particles P-9 of Experimental Example 8, lane 2 indicates proteins trapped by the probe-bonded particles which were prepared by using the carrier polymer particles P-10 of Experimental Example 9, lane 3 indicates proteins trapped by the probe-bonded particles which were prepared by using the magnetic particles of Comparative Example 4, lane 4 indicates the target material (AFP) 20 ng which is a control, lane 5 indicates the target material (AFP) 50 ng which is a control, lane 6 indicates the target material (AFP) 100 ng which is a control, and lane 7 indicates a molecular weight marker.

It can be understood from FIG. 3 that by using the probe-bonded particles which were prepared by using the polymer-bonded particles P-9 of Experimental Example 8, only the target material (AFP) band was collected from the serum in an amount of 11 ng per 0.2 mg of the particles. By using the antibody-bonded particles which were prepared by using the polymer-bonded particles P-10 of Experimental Example 9, only the target material (AFP) band was collected from the serum in an amount of 15 ng per 0.2 mg of the particles. On the other hand, although a number of bands of blood serum proteins nonspecifically collected were confirmed in the particles of Comparative Example 4, it was difficult to confirm the target AFP band.

The probe-bonded particles of Experimental Examples 8 and 9 were thus confirmed to exhibit only small nonspecific protein adsorption. Based on these results, it can be understood that since the surface of the particles is covered with a saccharide and the probe to specifically trap the target compound chemically bonds to the saccharide, the probe-bonded particles of Experimental Examples 8 and 9 exhibit only small nonspecific protein adsorption. On the other hand, the magnetic particles of Comparative Example 4 exhibited large nonspecific adsorption of proteins. It can thus be understood that the nonspecific adsorption is large if the surface of the particles is not covered with a saccharide.

4-3. Example 3
4-3-1. Evaluation Method
4-3-1A. Evaluation 1 of Nonspecific Adsorption (Evaluation of Nonspecific Adsorption of Proteins)
4-3-1A-1. Pre-Washing Step The carrier polymer particles prepared in the later-described Experimental Examples and Comparative Examples were diluted with and dispersed in purified water to obtain dispersion liquids, each having a particle concentration of 1 wt %. 500 microliters of the dispersion liquid was put into a microcentrifuge tube ("Safe-Lock tube" manufactured by Eppendorf) and centrifuged (15,000 rpm, 15° C., 10 minutes) using a centrifugal separator ("MX-150" manufactured by Tomy Seiki Co.) to remove the supernatant liquid. 500 microliters of a PBS(−) buffer solution was added to the tube which contained a precipitate, and the mixture was vibrated by a touch mixer to disperse the particles.

4-3-1A-2. Protein Adsorption Reaction Step

Then, 500 microliters of a PBS(−) solution of 1 wt % BSA (bovine serum albumin) was added to the tube and the mixture was vibrated by a touch mixer to disperse the particles in the solution, followed by mixing by rotation and inversion for two hours at room temperature.

4-3-1A-3. Washing Step

After centrifugal separation, the supernatant liquid was removed. 1 ml of 10 mM HEPES was added to the tube and the particles were dispersed by vibration using a touch mixer. After further repeating the same procedure twice, the content was transferred to another microcentrifuge tube to perform centrifugal separation, and the supernatant liquid was removed.

4-3-1A-4. Detaching Step

After the addition of 50 microliters of a 0.5% aqueous solution of SDS (sodium dodecylsulfate), the mixture was gently vibrated by a touch mixer to disperse the particles. After allowing the mixture to stand for 10 minutes, the centrifugal separation was performed and 20 microliters of the supernatant liquid was collected.

4-3-1A-5. Sampling Step 2-mercaptoethanol was dissolved in a premix sample buffer solution manufactured by Bio-Rad Laboratories, Inc. to a concentration of 2 wt % (this solution is hereinafter referred to as "sample buffer"). 20 microliters of the solution was collected in the microcentrifuge tube. 20 microliters of the supernatant liquid collected in the above step was mixed and heated at 100° C. for five minutes in a tube heater.

As controls, a 1 wt % BSA solution in PBS(−) was diluted with 2% SDS to 5,000 fold, 10,000 fold, and 20,000 fold. 20 microliters of each of the diluted solutions was mixed with 20 microliters of the sample buffer and heated in a tube heated at 100° C. for five minutes. The resulting solutions are called reference BSA dilutions.

4-3-1A-6. Electrophoresis (SDS-PAGE)

The reference AFP dilutions were applied to a vertical electrophoresis system ("Mini-PROTEAN3" manufactured by Bio-Rad Laboratories, Inc.) in an amount of 20 microliters per one lane to perform electrophoresis using a precast polyacrylamide gel ("Ready Gel J" (15%) manufactured by Bio-Rad Laboratories, Inc.) and a premix electrophoresis buffer solution manufactured by Bio-Rad Laboratories, Inc. The gel was stained by a standard staining method using "Silver Stain Plus Kit" manufactured by Bio-Rad Laboratories, Inc. The stained gel was scanned using a densitometer "GS-700" manufactured by Bio-Rad Laboratories, Inc. to produce an image. The product of the concentration and the area of the BSA band in the gel were determined using an analysis software "Multi-Analyst".

Since the weight of BSA which flows per one lane of the gel is known in the dilution BSA for reference, a calibration curve was drawn from the product of the band concentration and the area, and the amount of BSA detached from the particles was converted on a weight basis based on the calibration curve. The resulting weight corresponded to the amount of BSA which had been adsorbed per one mg of the particles.

4-3-1B. Evaluation of Specific Trapping Property 4-3-1B-1. Preparation of Probe-bonded Polymer Particles Carrier polymer particles prepared in the later-described Experimental Examples and Comparative Examples were diluted with and dispersed in purified water to obtain dispersion liquids, each having a particle concentration of 1 wt %. 500 microliters of the water dispersion was put into a microcentrifuge tube and centrifuged to remove the supernatant liquid. After washing three times with a 50 mM MES-NaOH buffer solution (pH 6, hereinafter referred to as "Buffer-1"), 0.8 mg of N-hydroxysuccinic acid imide (NHS) and 0.88 mg of 1-ethyl-3-(3-dimethylaminopropyl)carbodiimide (EDC) were added and stirred. Then, 0.05 mg of a protein (anti-alpha-fetoprotein antibody) which acts as a probe for specifically catching the target material (alpha-fetoprotein, hereinafter referred to from time to time as "AFP") was added and the mixture was stirred at room temperature for two hours. After the reaction, the particles were separated by centrifugal separation and the supernatant liquid was removed. Then, 500 microliters of a PBS (−) buffer solution containing 1% ethanol amine was added and the mixture was stirred at room temperature for two hours. Furthermore, after washing five times with a PBS (−) buffer solution, the particles were dispersed in 500 microliters of PBS (−) buffer solution to obtain a dispersion liquid of probe (antibody)-bonded particles.

4-3-1B-2. Target Material (Protein) Adsorption Reaction Step 100 microliters of the above dispersion liquid of the probe-bonded particles was sampled in a separate tube. The particles were separated by centrifugation to remove the supernatant liquid. 500 microliters of a human blood serum solution containing the target protein (human alpha-fetoprotein (AFP)) which is the target material was added to the particles. The mixture was vibrated by a touch mixer to disperse the particles in the solution, followed by mixing by rotation and inversion for two hours at room temperature.

4-3-1B-3. Washing Step

After centrifugal separation, the supernatant liquid was removed. 1 ml of 10 mM HEPES was added to the tube and the particles were dispersed using a touch mixer. After further repeating the same procedure twice, the content was transferred to another microcentrifuge tube to perform centrifugal separation, and the supernatant liquid was removed.

4-3-1B-4. Detaching Step

After the addition of 50 microliters of a 0.5% aqueous solution of SDS (sodium dodecylsulfate), the mixture was gently vibrated by a touch mixer to disperse the particles. After allowing the mixture to stand for 10 minutes, the centrifugal separation was performed and 20 microliters of a supernatant liquid was collected.

4-3-1B-5. Sampling Step 2-mercaptoethanol was dissolved in a premix sample buffer solution manufactured by Bio-Rad Laboratories, Inc. to a concentration of 2 wt % (this solution is hereinafter referred to as "sample buffer"). 20 microliters of the solution was collected in the microcentrifuge tube. 20 microliters of the supernatant liquid collected in the above step was mixed and heated at 100° C. for five minutes in a tube heater.

As controls, a 1 mg/ml AFP/PBS (−) solution was diluted with an SDS solution to 100 fold, 200 fold, and 500 fold. 20 microliters of each of the diluted solutions was mixed with 20 microliters of the sample buffer and heated by a block heater at 100° C. for five minutes. The resulting solutions are called reference AFP dilutions.

4-3-1B-6. Electrophoresis (SDS-PAGE)

The electrophoresis was carried out in the same manner as in 4.1.1F except for using AFP instead of BSA.

Since the weight of AFP which flows per one lane of the gel is known in the reference dilution AFP, a calibration curve was drawn from the product of the concentration and the area of the band, and the amount of AFP detached from the particles was converted on a weight basis based on the calibration curve. The resulting weight corresponded to the amount of AFP which had been adsorbed per 0.2 mg of the particles.

4-3-1C. Particle Diameter

The diameter of the particles with a diameter of 1 micrometer or more was measured using a laser diffraction particle size distribution analyzer ("SALD-200V" manufactured by Shimadzu Corp.) and the diameter of the particles with a diameter of less than 1 micrometer was measured using a particle size distribution analyzer based on a laser dispersion diffraction method ("LS 13 320" manufactured by Beckmann Coulter).

4-3-1D. Infrared Absorption Spectrum

The infrared absorption spectrum was measured by a KBr method using a Fourier-transform infrared spectrophotometer ("JIR-5500" manufactured by JEOL Ltd.).

4-3-2. Synthesis Examples 4-3-2A. Synthesis Example 12 (Synthesis of Organic Polymer Particles A-8)

The organic polymer particles A-8 were prepared by a two-step swelling polymerization method using seed particles.

Using polystyrene particles with a particle diameter of 0.98 micrometers obtained by soap-free polymerization as seed particles, a water dispersion (solid content: 5.0 g) was prepared by dispersing these polystyrene particles in 500 g of water in a nitrogen atmosphere. According to the two step swelling polymerization method (based on the method described in JP-B-57-24369), an organic solvent (0.1 g of "Shellsol TK") was added to the seed particles as a first step, and monomers (10 g of TMP (trimethylolpropane trimethacrylate) and 90 g of GMA (glycidyl methacrylate)) were added as a second step to cause them to be adsorbed. Then, 2 g of AIBN (azobisisobutyronitrile) was added and the mixture was slowly stirred at 75° C. for 24 hours. The reaction solution was cooled and filtered through a 500 mesh wire gauze to confirm that 99% of the product passed through the wire gauze. The polymerization stability was good. The polymerization yield was 99%. The particle diameter of the resulting organic polymer particles A-8 was 2.58 micrometers, the coefficient of variation of the particle diameter was 2.3%, and the particles were monodisperse particles.

4-3-2B. Synthesis Example 13 (Synthesis of Organic Polymer Particles A-9)

Organic polymer particles A-9 with a particle diameter of 2.61 micrometers and a coefficient of variation of 2.1% were obtained in the same manner as in Synthetic Example 12, except for using 30 g of MMA, 10 g of TMP, and 60 g of GMA as monomers.

4-3-2C. Synthesis Example 14 (Synthesis of Saccharide CMC-1)

Diluted hydrochloric acid was added to an aqueous solution of carboxymethylcellulose sodium salt ("APP-84" manufactured by Nippon Paper Chemicals Co., Ltd., a compound having an average molecular weight of 17,000 and an average of 0.7 carboxyl groups per one glucose unit) until the solution has a pH of 2 or less. The resulting solution was dialyzed and concentrated to obtain a 1% aqueous solution of carboxymethylcellulose CMC-1.

4-3-3. Experimental Example 10

4-3-3A. Preparation of Carrier Polymer Particles P-11

The polymer particles isolated from the dispersion liquid of organic polymer particles A-8 by centrifugation were washed by dispersing in acetone, followed by centrifugation. This washing procedure was repeated three times. The resulting particles were dried. 0.50 g of the particles was put into a 200 ml flask and 5 g of acetone and 75 g of 1% sulfuric acid were added. Particles were irradiated with indirect ultrasonic radiation for 20 minutes and dispersed. The dispersion liquid was heated at 60° C. for two hours while stirring, followed by isolation of the particles by centrifugal separation. The particles were washed three times with water and dried to obtain 0.51 g of organic polymer particles Hy-1 as a white powder.

The weight of the organic polymer particles Hy-1 was larger than the weight of the organic polymer particles A-8. Comparison of the infrared absorption spectrum of the organic polymer particles Hy-1 (after sulfuric acid treatment) with the infrared absorption spectrum of the organic polymer particles A-8 (before sulfuric acid treatment) indicates that in the infrared absorption spectrum of the organic polymer particles Hy-1, a peak originating from an epoxy group, which was observed around 900 $cm^{-1}$ of the infrared absorption spectrum of the organic polymer particles A-8, was weak and, instead, a broad peak due to a hydroxyl group was observed around 3,500 $cm^{-1}$. Based on the above results, the organic polymer particles Hy-1 were confirmed to have been obtained by a partial hydrolysis of epoxy groups in the organic polymer particles A-8 and introduction of hydroxyl groups.

0.50 g of the organic polymer particles Hy-1 was put into a 100 ml flask and 25 g of ethylenediamine was added. Particles were irradiated with indirect ultrasonic radiation for 10 minutes and dispersed. The dispersion liquid was stirred at 50° C. in a nitrogen atmosphere for six hours, followed by isolation of the particles by centrifugal separation. The particles were washed four times with methanol and dried to obtain 0.61 g of organic polymer particles Am-8 as a white powder.

The weight of the organic polymer particles Am-8 was larger than the weight of the organic polymer particles Hy-1. Comparison of the infrared absorption spectrum of the organic polymer particles Am-8 (after ethylenediamine treatment) with the infrared absorption spectrum of the organic polymer particles Hy-1 (before ethylenediamine treatment) indicates that in the infrared absorption spectrum of the organic polymer particles Am-8, a peak originating from an epoxy group, which was observed around 900 $cm^{-1}$ of the infrared absorption spectrum of the organic polymer particles Hy-1, disappeared and, instead, peaks typical to primary amine appeared around 3,300 $cm^{-1}$ and 3,500 $cm^{-1}$. Based on the results, the organic polymer particles Am-8 were confirmed to have an amino group introduced into the organic polymer particles Hy-1.

6 mg of N-hydroxysuccinic acid imide was added to 3 g of a 1% aqueous solution of CMC-1 which was obtained in Synthetic Example 14, and the mixture was stirred at room temperature for 10 minutes. Next, the solution was cooled with ice and 20 mg of 1-ethyl-3-(3-dimethylaminopropyl) carbodiimide hydrochloride was added. The mixture was stirred under ice cooling for 30 minutes. Next, 30.1 mg of the above organic polymer particles Am-8 was added to the solution. The mixture was irradiated with indirect ultrasonic radiation for 20 minutes and stirred under ice cooling for 12 hours. The particles were isolated by centrifugal separation, dispersed in purified water, isolated by centrifugal separation, and washed. This procedure was repeated 10 times, followed by drying to obtain 35.0 mg of carrier polymer particle precursor pre-P-11.

In addition to the peaks originating from the organic polymer particles Am-8 before the reaction, peaks originating from carboxymethylcellulose were observed around 3,400 $cm^{-1}$ and 1,600 $cm^{-1}$ in the infrared absorption spectrum of the carrier polymer particle precursor pre-P-11. Based on these results, the carrier polymer particle precursor pre-P-11 was confirmed to have a saccharide (carboxymethylcellulose) bonded to the organic polymer particles Am-8.

An operation of dispersing the carrier polymer particle precursor pre-P-11 (20.2 mg) in 2 ml of a 0.01 M sodium hydroxide aqueous solution and isolating the particles by centrifugation was carried out three times, then an operation of dispersing the particles in purified water and isolating by centrifugal separation was carried out three times, followed by drying to obtain 18.6 mg of carrier polymer particles P-11.

The peaks originating from carboxymethylcellulose were still observed around 3,400 $cm^{-1}$ and 1,600 $cm^{-1}$ in the infrared absorption spectrum of the carrier polymer particles P-11, although these peaks were weaker as compared with those in the carrier polymer particle precursor pre-P-11 before the reaction. The carrier polymer particles P-11 were thus confirmed to have a saccharide (carboxymethylcellulose) bonded to the organic polymer particles Am-8. The carrier polymer particles P-11 were further treated with a 0.01 M aqueous solution of sodium hydroxide to find that the weight loss was less than 0.1 mg, which is a negligible amount.

4-3-3B. Evaluation Result of Nonspecific Absorption of Protein

The nonspecific protein adsorption of the carrier polymer particles P-11 was measured according the above-described method to confirm that the value was less than the detectable limit (0.01 ng/mg).

4-3-4. Experimental Example 11
4-3-4A. Preparation of Carrier Polymer Particles P-12

The polymer particles isolated from the dispersion liquid of organic polymer particles A-9 by centrifugation were washed by dispersing in acetone, followed by centrifugation. This washing procedure was repeated three times. The resulting particles were dried. 0.50 g of the particles were put into a 100 ml flask and 25 g of ethylenediamine was added. Particles were irradiated with indirect ultrasonic radiation for 10 minutes and dispersed. The dispersion liquid was stirred at 50° C. in a nitrogen atmosphere for six hours, followed by isolation of the particles by centrifugal separation. The particles were washed four times with methanol and dried to obtain 0.61 g of organic polymer particles Am-9 as a white powder. 29.9 mg of the organic polymer particles Am-9 was added to 3 g of a 1% aqueous solution of CMC-1 which was obtained in Synthetic Example 14. The mixture was irradiated with indirect supersonic wave for 20 minutes to disperse the particles. Next, the solution was cooled with ice and 20 mg of 1-ethyl-3-(3-dimethylaminopropyl)carbodiimide hydrochloride was added. The mixture was stirred under ice cooling for 12 hours. The procedure of isolation and drying was carried out in the same manner as in Experimental Example 10 to obtain 36.2 g of carrier polymer particle precursor pre-P-12. Next, the procedure of Experimental Example 10 was followed, except for using carrier polymer particle precursor pre-P-12 (20.3 mg) instead of the carrier polymer particle precursor pre-P-11 of the Experimental Example 10, to obtain 17.9 mg of carrier polymer particle precursor pre-P-12.

4-3-4B. Evaluation of Nonspecific Adsorption

The nonspecific protein adsorption of the carrier polymer particles P-12 was measured according the above-described method to confirm that the value was very low (0.02 ng/mg).

4-3-5. Comparative Example 5

The nonspecific protein adsorption of the organic polymer particles A-8 was measured according the above-described method to confirm that the value was high (1.1 ng/mg).

4-3-6. Comparative Example 6

Commercially available standard polystyrene particles ("STADEX SC200S" manufactured by JSR Corporation) was sufficiently washed with purified water and their nonspecific protein adsorption was measured according the above-described method to confirm that the value was very high (20 ng/mg).

4-3-7. Comparative Example 7

The nonspecific protein adsorption of the carrier polymer particle precursor pre-P-11 was measured according the above-described method to confirm that the value was very low (0.02 ng/mg), but not lower than that of the carrier polymer particles P-11, of which the nonspecific protein adsorption was less than the detectable limit 4-3-8. Evaluation Result of Specific Trapping Property FIG. 4 is a photograph showing the evaluation results of the specific trapping property (an electrophoresis pattern of proteins adsorbed on the probe-bonded particles) of carrier polymer particles P-11 and P-12 obtained respectively in Experimental Examples 10 and 11, and the carrier polymer particle precursor pre-P-11 obtained in Comparative Example 7

Figure 4:
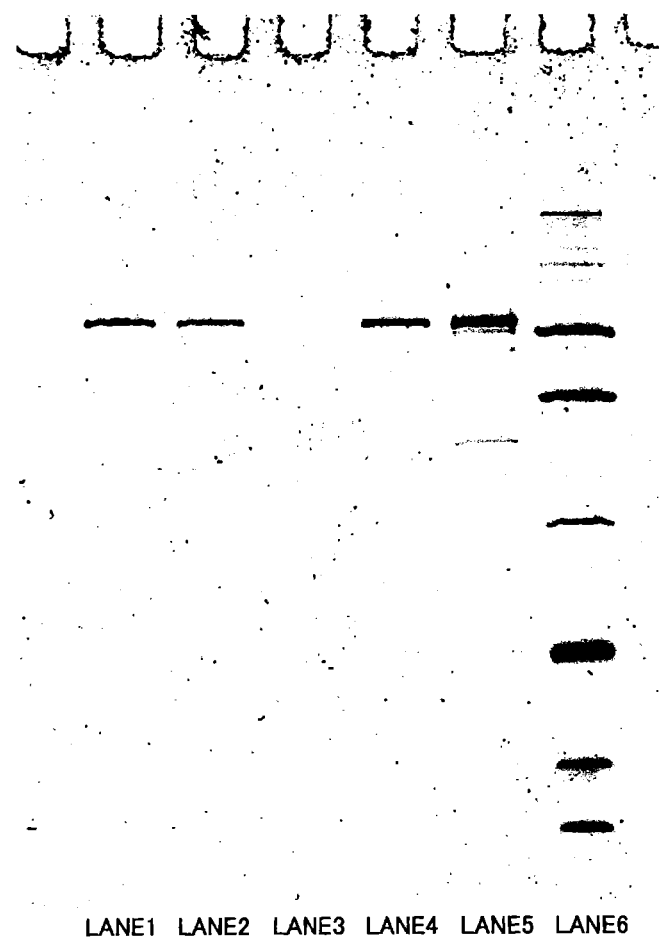
FIG. 4 is a photograph showing the specific trapping evaluation results of the probe-bonded particles obtained in Experimental Examples 10 and 11, and Comparative Example 7 (electrophoresis pattern of the proteins adsorbed on the probe bonding particles).

In FIG. 4, lane 1 indicates proteins trapped by the probe-bonded particles which were prepared by using the carrier polymer particles P-11 of Experimental Example 10, lane 2 indicates proteins trapped by the probe-bonded particles which were prepared by using the carrier polymer particles P-12 of Experimental Example 11, lane 3 indicates proteins trapped by the probe-bonded particles which were prepared by using the carrier polymer particle precursor pre-P-11 of Comparative Example 7, lane 4 indicates the target material (AFP) 20 ng which is a control, lane 5 indicates the target material (AFP) 50 ng which is a control, and lane 6 indicates a molecular weight marker.

It can be understood from FIG. 4 that using the probe-bonded particles which were prepared by using the carrier polymer particles P-11 of Experimental Example 10, only the target material (AFP) band was collected from the serum in an amount of 16 ng per 0.2 mg of the particles. By using the antigen-bonded particles which were prepared by using the polymer-bonded particles P-12 of Experimental Example 11, only the target material (AFP) band was collected from the serum in an amount of 12 ng per 0.2 mg of the particles. On the other hand, it was difficult to confirm the target AFP band in the particles of Comparative Example 7.

As a result of the above experiments, the probe-bonded particles formed using the carrier polymer particles of Experimental Examples 10 and 11 were confirmed to exhibit only small nonspecific protein adsorption and to be able to specifically trap the target material. On the other hand, the magnetic particles of Comparative Example 7 could not specifically trap a target material, although the particles exhibited small nonspecific protein adsorption. It can thus be understood that the particles with a physically-adsorbed saccharide on the surface covered with a saccharide, such as in the particles of Comparative Example 7, cannot exhibit sufficient nonspecific trapping performance of a target material.

The invention claimed is:

1. A process for producing carrier polymer particles, the process comprising:

reacting an organic polymer particle precursor with a diamine to form organic polymer particles comprising a first functional group; then reacting the first functional group of the organic polymer particles with a second functional group of a saccharide, thereby covering a surface of the organic polymer particles with the saccharide to form surface-covered organic polymer particles; and then chemically bonding a probe for specifically trapping a target material to the saccharide of the surface-covered organic polymer particles, to form carrier polymer particles, wherein the organic polymer particles have a particle diameter of 0.1 to 20 micrometers.

2. The process according to claim 1, wherein the first functional group is at least one selected from the group consisting of a carboxyl group, an epoxy group, an amino group, and a tosyl group.

3. The process of claim 1, further comprising:

extracting saccharide physically adsorbed on the surface of the surface-covered organic polymer particles by treating the surface-covered organic polymer particles with a basic solution.

4. The process according to claim 1, wherein the saccharide is a polysaccharide.

5. The process according to claim 1, wherein the chemical bonding of the probe to the saccharide forms at least one amide bond.

6. The process according to claim 1, wherein the first functional group is an amino group.

7. The process of claim 1, wherein the organic polymer particles are magnetic particles.

8. The process of claim 1, wherein the second functional group is a carboxymethyl group.

* * * * *

UNITED STATES PATENT AND TRADEMARK OFFICE
CERTIFICATE OF CORRECTION

PATENT NO. : 9,447,232 B2
APPLICATION NO. : 13/763236
DATED : September 20, 2016
INVENTOR(S) : Masayuki Takahashi et al.

It is certified that error appears in the above-identified patent and that said Letters Patent is hereby corrected as shown below:

On the Title Page

Item (71), the Applicant's information is incorrect. Item (71) should read:
-- (71) Applicant: JSR CORPORATION, Minato-ku (JP) --

Signed and Sealed this
Thirteenth Day of March, 2018

Andrei Iancu
*Director of the United States Patent and Trademark Office*